(12) United States Patent
Johnson et al.

(10) Patent No.: US 12,311,125 B2
(45) Date of Patent: May 27, 2025

(54) MEDICAL DEVICES WITH MULTI-PLANE ARTICULATION

(71) Applicant: Medtronic, Inc., Minneapolis, MN (US)

(72) Inventors: Kristin M. Johnson, Circle Pines, MN (US); Gregory N. Nesseth, Forest Lake, MN (US); Jonathan E. Baxter, Fridley, MN (US); Thomas A. Wong, Little Canada, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 17/393,046

(22) Filed: Aug. 3, 2021

(65) Prior Publication Data
US 2022/0040452 A1 Feb. 10, 2022

Related U.S. Application Data

(60) Provisional application No. 63/130,321, filed on Dec. 23, 2020, provisional application No. 63/061,787, filed on Aug. 5, 2020.

(51) Int. Cl.
*A61M 25/01* (2006.01)
*A61M 25/00* (2006.01)
(Continued)

(52) U.S. Cl.
CPC .... *A61M 25/0147* (2013.01); *A61M 25/0009* (2013.01); *A61M 25/0026* (2013.01);
(Continued)

(58) Field of Classification Search
CPC .......... A61M 25/0147; A61M 25/0009; A61M 25/0026; A61M 25/09041; A61B 1/0057
See application file for complete search history.

(56) References Cited

U.S. PATENT DOCUMENTS

| | | |
|---|---|---|
| 5,472,017 A | 12/1995 | Kovalcheck |
| 6,458,107 B1 | 10/2002 | Ockuly |

(Continued)

FOREIGN PATENT DOCUMENTS

| | | |
|---|---|---|
| WO | 2017/062514 | 4/2017 |
| WO | 2019/195287 | 10/2019 |

OTHER PUBLICATIONS

Baxter et al., U.S. Appl. No. 63/001,832, filed Mar. 30, 2020.
(Continued)

*Primary Examiner* — Joel M Attey
*Assistant Examiner* — John A Doubrava
(74) *Attorney, Agent, or Firm* — Mueting Raasch Group

(57) ABSTRACT

Medical devices that provide for selected curve deflection in multiple planes such that three-dimensional shapes can be formed in the medical devices by placing a pull wire extending through the catheter in tension, as well as methods of manufacturing and using the medical devices. The medical devices may include selected portions in which the location of the pull wire changes circumferentially and/or radially to provide for the selected curve deflection. The medical devices may include, in addition to, or in place of changes in pull wire location, selected portions having exhibiting changes in rigidity to provide for the selected curve deflection.

12 Claims, 16 Drawing Sheets

(51) Int. Cl.
    *A61M 25/09*     (2006.01)
    *B29C 64/255*     (2017.01)
    *B29C 64/295*     (2017.01)
    *B29C 64/321*     (2017.01)
    *B29C 64/393*     (2017.01)
    *B33Y 30/00*     (2015.01)
    *B33Y 80/00*     (2015.01)
    *A61N 1/372*     (2006.01)
    *B29C 64/118*     (2017.01)

(52) U.S. Cl.
    CPC ..... *A61M 25/09041* (2013.01); *B29C 64/255* (2017.08); *B29C 64/295* (2017.08); *B29C 64/321* (2017.08); *B29C 64/393* (2017.08); *B33Y 30/00* (2014.12); *B33Y 80/00* (2014.12); *A61M 2205/0216* (2013.01); *A61M 2205/0222* (2013.01); *A61N 1/372* (2013.01); *B29C 64/118* (2017.08)

(56) References Cited

U.S. PATENT DOCUMENTS

| | | |
|---|---|---|
| 6,907,298 B2 | 6/2005 | Smits et al. |
| 2002/0082585 A1 | 6/2002 | Carroll et al. |
| 2003/0135156 A1* | 7/2003 | Bencini ............ A61M 25/0144 604/95.04 |
| 2014/0236120 A1 | 8/2014 | Tsai et al. |
| 2015/0094735 A1 | 4/2015 | Ward et al. |
| 2016/0346503 A1 | 12/2016 | Jackson |
| 2020/0155798 A1 | 5/2020 | Yang et al. |
| 2021/0122115 A1 | 4/2021 | Ramos |
| 2022/0379079 A1* | 12/2022 | Richter ................ A61N 1/056 |

OTHER PUBLICATIONS

Baxter et al., U.S. Appl. No. 63/059,867, filed Jul. 31, 2020.
Baxter et al., U.S. Appl. No. 63/059,890, filed Jul. 31, 2020.
Baxter et al., U.S. Appl. No. 17/215,842, filed Mar. 29, 2021.
Baxter et al., U.S. Appl. No. 17/389,226, filed Jul. 29, 2021.
Baxter et al., U.S. Appl. No. 17/389,232, filed Jul. 29, 2021.
Ramos et al., U.S. Appl. No. 62/927,092, filed Oct. 28, 2019.
Ramos et al., U.S. Appl. No. 17/081,815, filed Oct. 27, 2020.
International Preliminary Report on Patentability for PCT/US2021/044367 dated Feb. 16, 2023 (12 pages).
International Preliminary Report on Patentability for PCT/US2021/044371 dated Feb. 16, 2023 (12 pages).
International Search Report and Written Opinion for PCT/US2021/044367, mailed Jan. 10, 2022. 19 pages.
International Search Report and Written Opinion for PCT/US2021/044371, mailed Jan. 11, 2022. 21 pages.

* cited by examiner

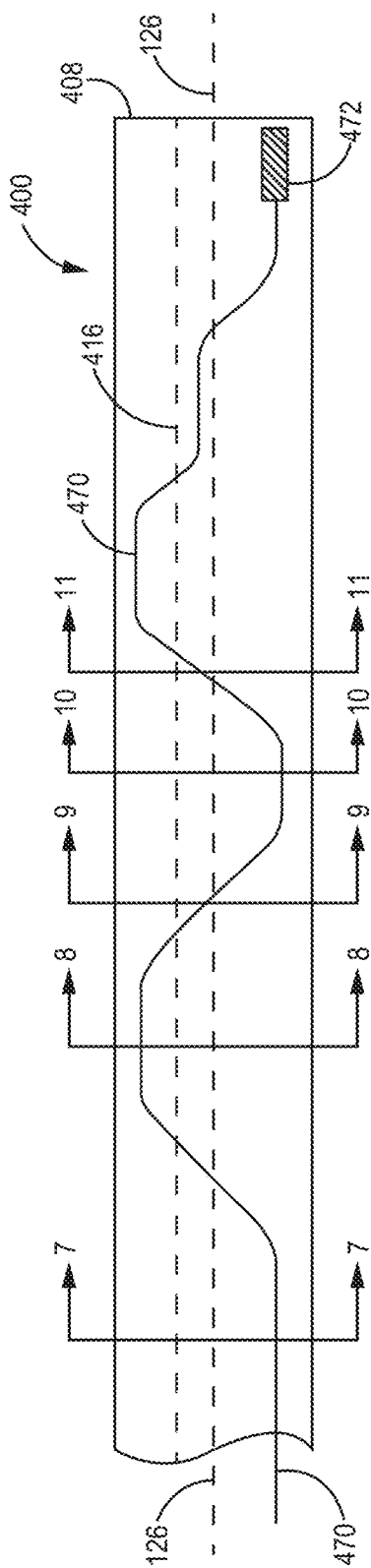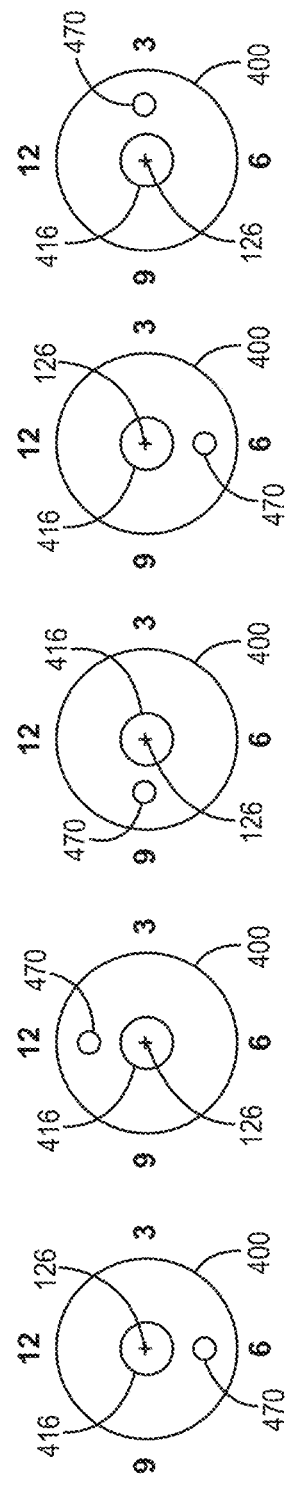

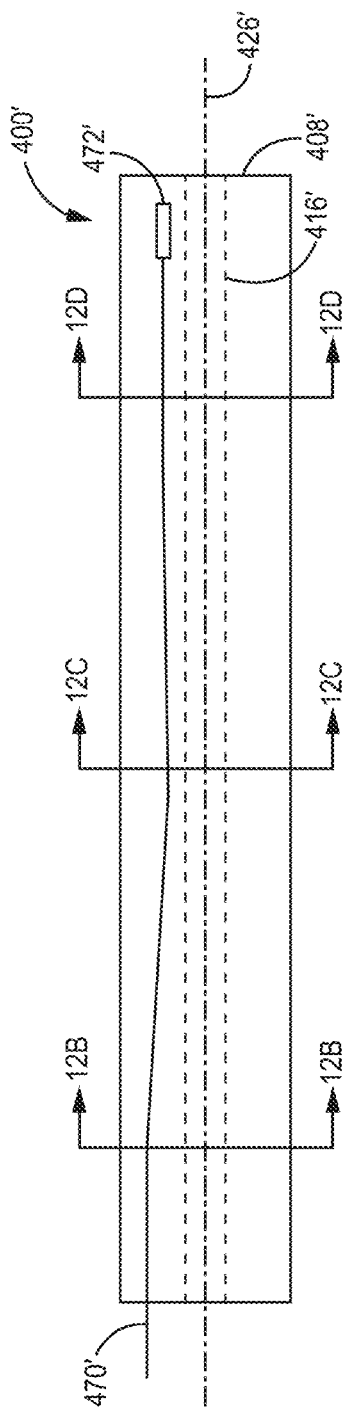
FIG. 12A
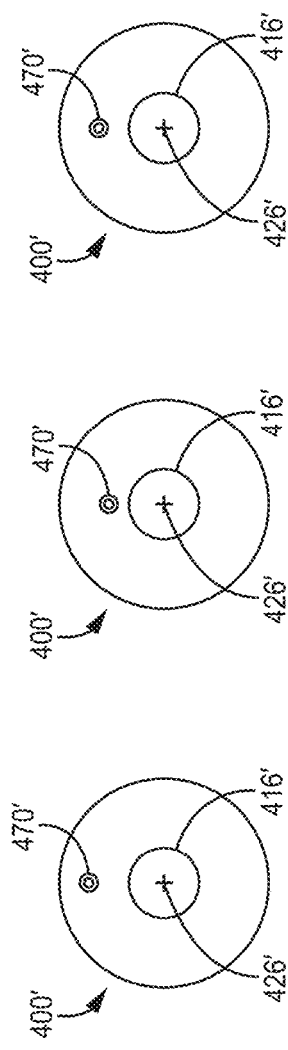
FIG. 12B
FIG. 12C
FIG. 12D

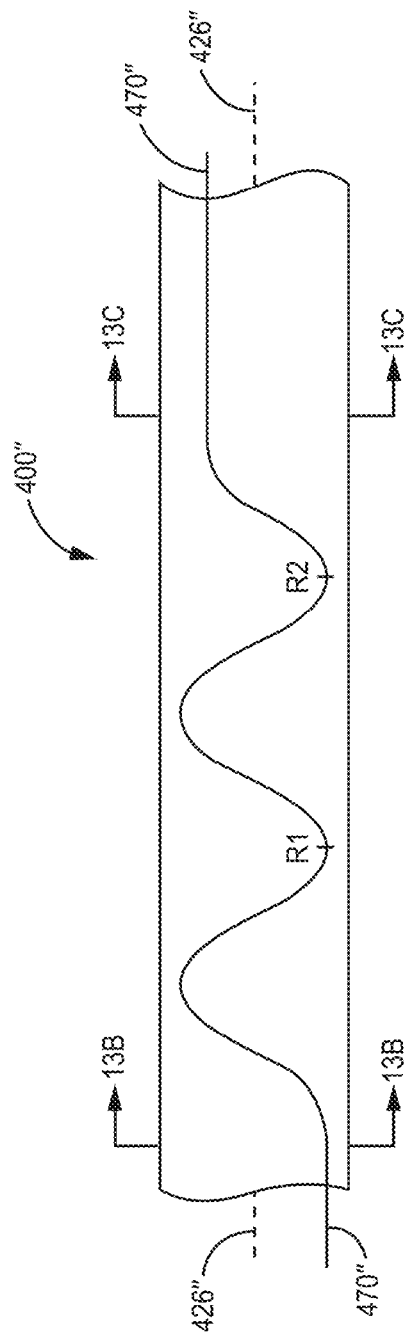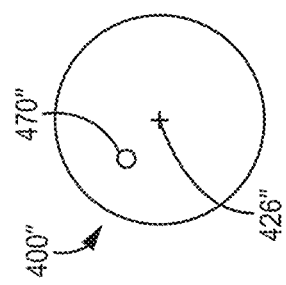

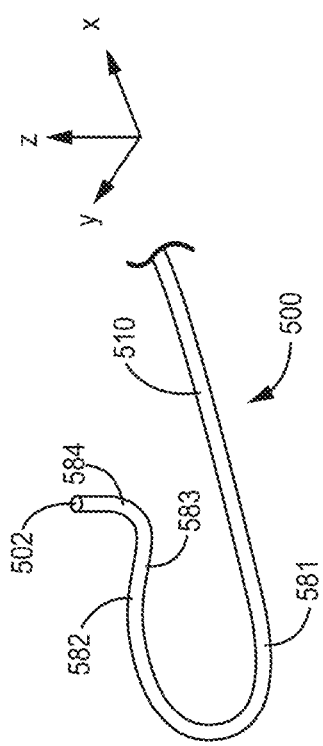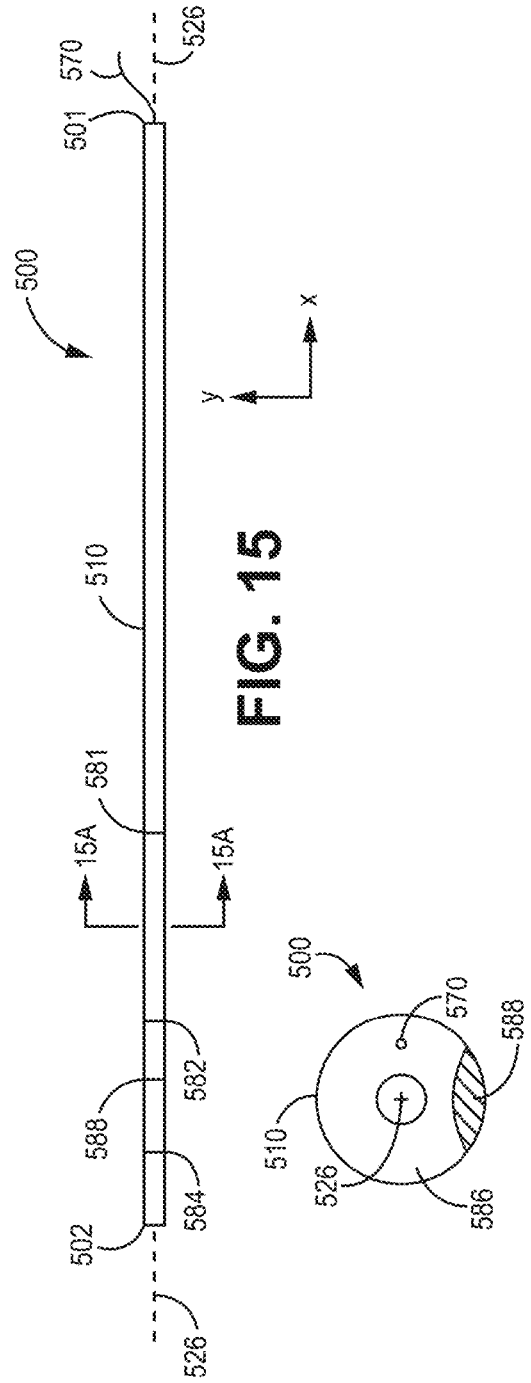

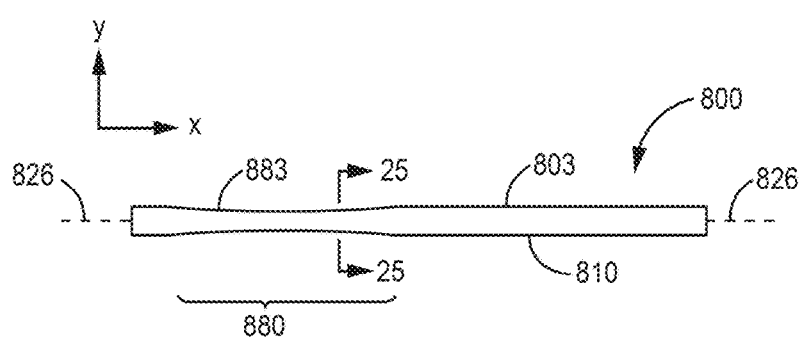
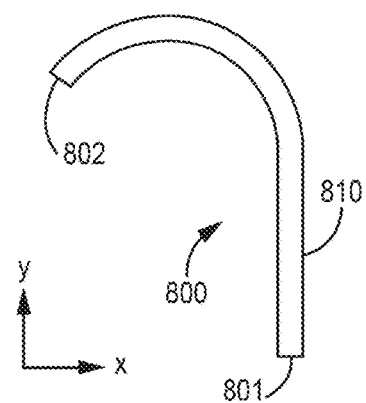
FIG. 23
FIG. 24
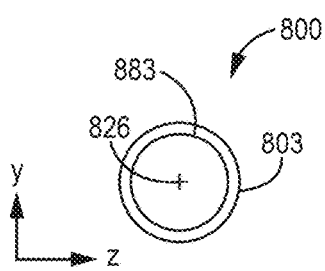
FIG. 25
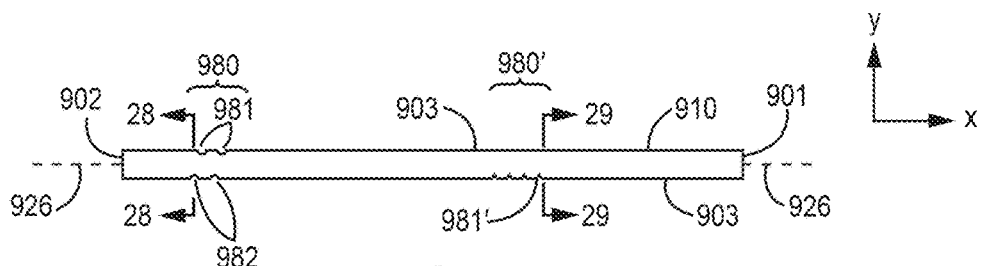
FIG. 26
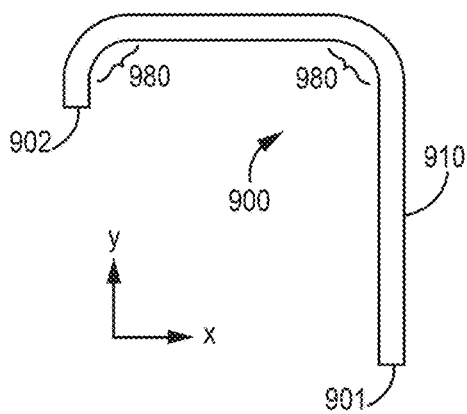
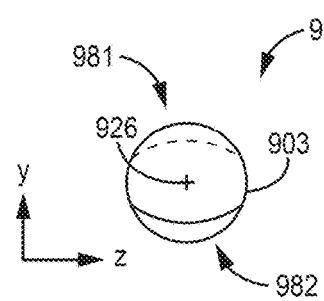
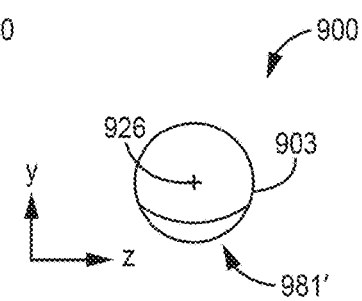
FIG. 27   FIG. 28   FIG. 29

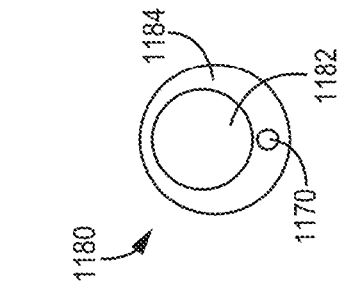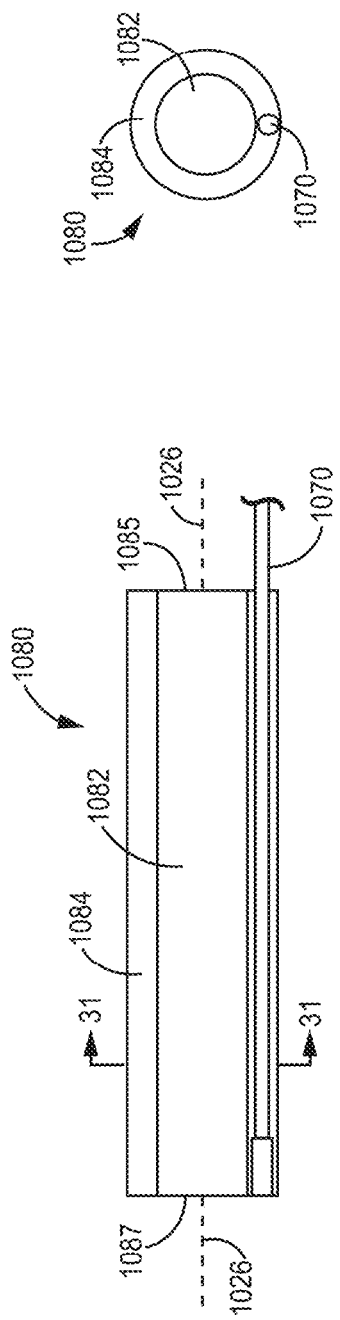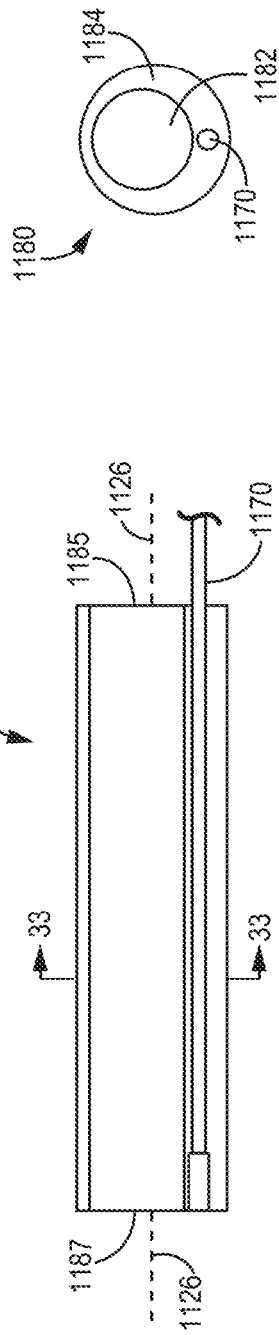

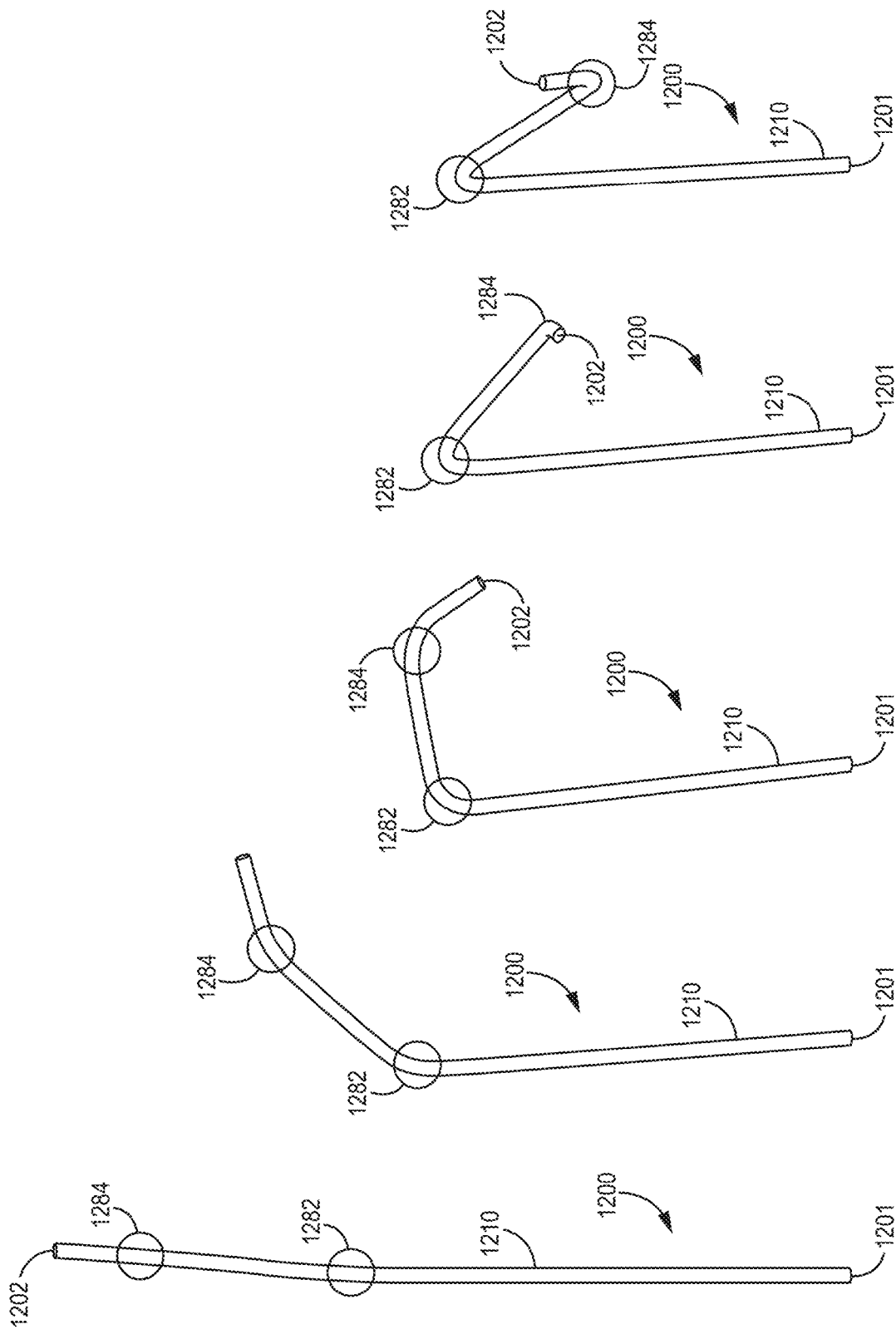

MEDICAL DEVICES WITH MULTI-PLANE ARTICULATION

CROSS-REFERENCE TO RELATED APPLICATIONS

This application claims the benefit under 35 U.S.C. § 119 of U.S. Provisional Application Ser. No. 63/061,787 filed 5 Aug. 2020 and titled MEDICAL DEVICES WITH MULTI-PLANE ARTICULATION USING A SINGLE PULL WIRE and also U.S. Provisional Application Ser. No. 63/130,321 filed 23 Dec. 2020, and titled MEDICAL DEVICES WITH MULTI-PLANE ARTICULATION, each of which is incorporated herein by reference in its entirety.

FIELD

The disclosure generally relates to medical devices and, in particular, additive manufacturing of 3D printed medical devices, such as catheters and implantable stimulation leads capable of deflection in multiple planes using a pull wire.

BACKGROUND

Medical catheters and leads are commonly used to access vascular and other locations within a body and to perform various functions at those locations, for example, delivery catheters may be used to deliver medical devices, such as implantable medical leads. A number of such medical devices are designed to be navigated through tortuous paths in a human body, such as through a patient's vasculature. Medical catheters and leads may be designed to be sufficiently flexible to move through turns, or curves, in the vasculature yet sufficiently stiff, or resilient, to be pushed through the vasculature. In many cases, such as those involving cardiovascular vessels, the route to the treatment or deployment site may be tortuous and may present conflicting design considerations that may require compromises between dimensions, flexibilities, material selection, operational controls and the like. These contrasting properties can present challenges in designing and manufacturing catheters. Existing manufacturing processes, such as conventional extrusion, may also limit options in designing and manufacturing catheters.

Catheters are shaped to reach anatomical locations in three main ways: (1) curve baking to heat set braid and polymer, (2) pull wires fixed distal to the articulation point, and (3) stylet driven shapes. A consistent 3D shape can be challenging to achieve, and catheters can utilize more than one of the shaping modes to get a needed overall shape and an articulation point required. Curve baking (1) generally requires placing the catheter into a mold or over a mandrel that has a shape and heating the catheter to set the shape. Curve baked shapes usually have to be shaped in a curve that is more dramatic than the desired final shape and removing the catheter and relaxing of the catheter can alter the shape. The distal components of a catheter are usually a lower durometer and interactions with anatomy as well as time in body temperature fluid may diminish shape retention on curve baked catheters. Pull wires are typically used in the form of a single wire for an articulation of a radius in one plane and are often combined with a shape set via curve baking.

SUMMARY

The present disclosure generally relates to medical devices (such as catheters and leads—both of which will be commonly referred to herein as catheters) that provide for selected curve deflection in multiple planes such that three-dimensional shapes can be formed in the catheters by placing a pull wire extending through the catheter in tension, as well as methods of manufacturing and using the medical devices.

In one or more embodiments of the medical devices described herein, the pull wire is anchored at a location distal from the portions of the catheter body desired to be deflected using the pull wire. A proximal end of the pull wire extends out of the catheter body at the proximal end of the catheter body to allow for manipulation of the pull wire as described herein. In one or more embodiments, the anchor, that is, the point at which the pull wire is fixed at a selected location within the catheter body, may be located at or near the distal end of the catheter body where, for example, the catheter body is to be deflected proximate the distal end (and/or anywhere proximal from the distal end of the catheter body). In other embodiments, the anchor may be located proximal from the distal end of the catheter body where, for example, deflection of the portion of the catheter body distal from the anchor is not required or desired.

In one or more embodiments, such deflection or motion of the catheter can be achieved by changing the location of the pull wire within the catheter body and, optionally, changing the rigidity of one or more portions of a catheter body. Moreover, varying the rate at which the location of the pull wire changes within the catheter body can also be used to provide selected characteristics in deflection of the catheter body as desired.

Changing the location of a pull wire within the catheter body relative a longitudinal axis extending through the catheter body at a fixed location can provide selected curve deflection in multiple planes such that three-dimensional shapes can be formed in the catheters when the pull wires located in the catheters are placed in tension sufficient to cause the catheters to deflect as described herein. The location of the pull wire may be described, for example, as changing relative to a central longitudinal axis extending through the geometric center of the catheter body (where the geometric center is determined relative to a cross-sectional shape of the catheter body taken transverse to the central longitudinal axis). The change in location or position of the pull wire may be radially and/or circumferentially as described herein.

Regarding changes in circumferential position of pull wires as described herein, the change in circumferential position can be controlled to, in one or more embodiments, provide controlled changes in circumferential position of the pull wires over the length of one or more selected portions of catheter bodies that are in increments as small as 1 degree (measured relative to a catheter axis as described herein). As a result, the circumferential positions of pull wires over the lengths of selected portions of the catheter bodies can be controlled to move over an arc of, e.g., 1 degree or more, 2 degrees or more, 3 degrees or more, 4 degrees or more, or 5 degrees or more at a low end. At the upper end, the pull wires may, in one or more embodiments, move circumferentially over an arc of X+(n*360) degrees or less, where X is 360 degrees or less, 330 degrees or less, 300 degrees or less, 270 degrees or less, 240 degrees or less, 210 degrees or less, 180 degrees or less, 150 degrees or less, 135 degrees or less, 120 degrees or less, 90 degrees or less, 75 degrees or less, 60 degrees or less, 45 degrees or less, 30 degrees or less, 15 degrees or less, 10 degrees or less, or 5 degrees or less over the lengths of the selected portions of the catheter bodies.

Even such relatively small changes in circumferential position yields improvements in forming selected curve deflections in multiple planes as described herein. These selected changes in circumferential position of pull wires can be distinguished from random variations in circumferential position of a pull wire that can occur during manufacturing of conventional catheter bodies. In those instances, the variations in circumferential position are random, i.e., not controlled and, essentially, a function of native (uncontrolled) forces present in the manufacturing process.

The selected portions of the catheter bodies over which the changes in circumferential and/or radial position of pull wires as described herein may, in one or more embodiments, have lengths that are limited to, for example, 50% or less, 40% or less, 30% or less, 20% or less, or 10% or less of the total lengths of the catheter bodies as measured from their proximal ends to their distal ends. In other words, the circumferential and/or radial pull wire position changes can be controlled over both relatively long and relatively short portions of the catheter bodies of catheters as described herein. In terms of specific lengths, in one or more embodiments, the lengths of the selected portions over which the circumferential and/or radial pull wire position changes occur can, at a lower end, be, e.g., 5 millimeters (mm) or more, 10 mm or more, 15 mm or more, or 20 mm or more. At an upper end, the lengths of the selected portions over which the circumferential and/or radial pull wire position changes occur can, in one or more embodiments, be, e.g., 200 mm or less, 160 mm or less, 120 mm or less, or 100 mm or less.

Selected curve deflection in multiple planes such that three-dimensional shapes can be formed in the catheters in response to placing pull wires located in the catheter bodies in tension as described herein may also be achieved by changing the rigidity (sometimes referred to as stiffness) of selected portions of the catheter body to achieve selected changes in the shape of the catheter when the pull wire is placed in tension along the length of the catheter. The changes in rigidity of selected portions of the catheter body can, alone, provide selected curve deflection in multiple planes, but those properties can potentially be enhanced by changing the location of a pull wire within the catheter body as described herein.

Rigidity/stiffness of a selected portion of a catheter body can, in one or more embodiments, be defined by the EI of the portion of the catheter body where "E" is modulus of elasticity of the materials making up the body and "I" is moment of inertia of the catheter body, with "I" being changeable based on the placement of the materials making up the selected portion of the catheter body.

In one or more embodiments, the catheter bodies of the catheters described herein include two or more portions in which the rigidity differs from surrounding portions of the catheter body such that the selected portions are either more or less resistant to bending or deflection when a pull wire extending through those portions is placed in tension. While the "E" values of the materials used to construct the catheter bodies are generally not changeable (at least in the additive manufacturing processes described herein), the composite "E" values of selected portions of the catheter bodies described herein can be selected by changing the relative volumes of the materials in each selected portion. For example, to increase the "E" value of a selected portion of a catheter body, the ratio of higher "E" value materials to lower "E" value materials in the selected portion of a catheter body can be increased. Conversely, to reduce the "E" value of a selected portion of a catheter body, the ratio of higher "E" value materials to lower "E" value materials in the selected portion of a catheter body can be decreased.

In addition to or in place of changing the "E" value of selected portions of catheter bodies of catheters as described herein to change rigidity, the placement of the materials making up the selected portions of the catheter bodies can be selected to increase or decrease the "I" value (moment of inertia) of the selected portions because the moment of inertia of a rigid composite system such as the selected portions of the catheter bodies is the sum of the moments of inertia of the components making up the selected portions of the catheter bodies. For example, selection and distribution of materials that, collectively, increase the "I" value in a selected portion of a catheter body will increase the rigidity ("H") of that portion of the body. Conversely, selection and distribution of materials that, collectively, decrease the "I" value in a selected portion of a catheter body will decrease the rigidity ("EI") of that portion of the body.

Although changes in the "I" value to achieve selected changes in the rigidity of selected portions of a catheter body as described herein can be achieved without changing the size (i.e., cross-sectional area) and/or shape of the catheter body, changes in the size/shape of the catheter body can also be used in combination with the selection and distribution of different materials making up the catheter body and/or the location of a pull wire to provide a catheter that exhibits selected deflection in multiple planes such that three-dimensional shapes can be formed by the catheters when a pull wire extending through the catheter is placed in tension.

Regardless of how changes in rigidity are achieved in the selected portions of the catheter bodies as described herein, the rigidity (i.e., composite EI value) of any selected portion of a given catheter body may be 90% or less, 75% or less, 50% or less, 40% or less, 30% or less, 20% or less, or even 10% or less of the rigidity (i.e., composite EI value) of a different selected portion of the given catheter body. The selected portions of the catheter bodies having lower rigidity values than other selected portions will typically form curves before selected portions having higher rigidity values when pull wires extending through the catheter bodies are placed in tension as described herein. In addition, the selected portions of the catheter bodies having lower rigidity values than other selected portions may form curves having different (e.g., smaller) radii of curvature than selected portions having higher rigidity values when pull wires extending through the catheter bodies are placed in tension as described herein (when the different selected portions have the same length).

Although additive manufacturing and the use of two or more different materials in an additive manufacturing process can be used to provide a selected rigidity to one or more selected portions of a catheter body as described herein, other more conventional components may be used in place of or in addition to materials provided in an additive manufacturing process. For example, one or more selected portions of one or more embodiments of catheter bodies as described herein may include braids, coils, filaments (wrapped or otherwise), etc. that may be used to either increase or decrease the rigidity of the one or more selected portions. Those components may be used in conjunction with a pull wire as described herein to provide a catheter that exhibits selected deflection in multiple planes such that three-dimensional shapes can be formed in the catheters by placing pull wires in the catheters in tension as described herein.

In one or more embodiments, the material or materials used to make up the catheter body and the location of the pull wire may all remain constant between adjacent portions of a catheter body, with only the size/shape of the catheter body changing to change the rigidity between those selected portions in a manner that results in selected deflection of the catheter in multiple planes such that three-dimensional shapes can be formed by the catheters by placing pull wires located in the catheters in tension as described herein.

Catheter bodies of catheters manufactured using the additive manufacturing processes described herein provide the opportunity to produce catheter bodies having selective rigidity in selected portions along the length of the catheters. When combined with pull wire placement, controlling the rigidity of selected portions of the catheter bodies of catheters as described herein is a powerful tool to provide catheters that can achieve curve deflection of the catheter in multiple planes such that three-dimensional shapes can be formed by the catheters by placing pull wires located in the catheters in tension as described herein. These properties are not available in conventional catheters.

Moreover, these properties can, in one or more embodiments, be achieved using a single pull wire extending through the catheter body as compared to known catheters that may use multiple pull wires to achieve selected deflection of different portions of a catheter in multiple planes and/or different directions (although it should be understood that the catheter bodies of catheters described herein may include one or more other pull wires in addition to the pull wires used to achieve the properties described herein).

The various properties of rigidity in each of the portions of the catheters described herein may be chosen to provide for a selected order of formation. In other words, the order in which the catheter body portions between the various locations form curves may be selected by tailoring the rigidity in each of the portions to achieve that function. For example, in one or more embodiments, the distal most portion of a catheter body configured to form a curve as described herein may be activated or curve before any portion or portions of the catheter body proximal to the distal most portion form a curve as described herein. In other embodiments, the rigidity of the selected portions of a catheter body that are configured to form a curve as described herein may be tailored such that the selected portions of the catheter body form those curves in a selected order, even in catheters in which only a single pull wire is used to supply the compressive force on the catheter body. In general, portions of the catheter bodies described herein that have a lower rigidity will form curves in response to tension delivered through a pull wire before other portions of the same catheter body that have a higher rigidity. That selective order of formation may offer catheters that are more able to advance through complex paths during advancement to a selected location within a patient.

In one or more embodiments, the selected portions of one or more embodiments of the catheters described herein in which curves may be formed (using, e.g., a pull wire as described herein) may be constructed that the catheter bodies forming the curves relax or reverse one or more of the curves formed during activation of the selected portions. Such relaxation or reversal may, in one or more embodiments, result in catheters in which one or more of the selected portions forming curves return to their original shapes, i.e., their shapes before the curves are formed in the selected portions. In one or more alternative embodiments, one or more of the curves formed by one or more of the selected portions may remain even after the force used to activate or form the curves is removed (e.g., a pull wire placed in tension to provide a compressive force to form the curves may be released such that the pull wire is no longer in tension). Curves remaining in the catheter body after removal of the force or forces used to form the curves may be the result of any of a number of forces, e.g., plastic deformation of the selected portion of the catheter body during curve formation, friction between layers and/or components in the selected portion that remains after the curve is formed, material properties such as hydrophobicity/hydrophilicity, phase changes made in phase change materials incorporated into the catheter bodies, the use of shape memory materials (e.g., nitinol, etc.), etc.

In one or more embodiments, friction used to retain one or more curves formed in a catheter as described herein may be provided in the form of friction in selected areas (e.g., curved portions, other selected portions adjacent and/or spaced apart from the curved portions, etc.) between pull wires and the lumens in which the pull wires are located. Friction between the pull wires and lumens may be controlled by changes in relative sizes and/or shapes of the pull wire and the lumen in which the pull wire is located (e.g., clearance between the pull wires and lumens may be increased or decreased in selected areas using changes in size and/or shape of the pull wire and/or lumen), changes in the surfaces of the pull wires and/or lumens (e.g., one or both of the surfaces may be modified to increase or decrease friction in selected areas, changes in materials may increase or decrease friction, etc.), deformation of the pull wires and/or lumens as curves are formed and/or released may also increase or decrease friction in selected areas along a catheter, etc. Pull wire friction can also be increased in selected portions of as catheter body by, e.g., increasing the wrap of the pull wire around the circumference of the catheter body within a selected portion, etc.).

In place of or in addition to tailoring the order of formation of curves in one or more embodiments of the catheters, the order of relaxation of two or more curves in a catheter as described herein may also be controlled using, e.g., plastic/elastic deformation of selected portions of the catheters, friction between layers and/or components of catheters as described herein, etc.

The medical devices described herein may be manufactured using additive manufacturing systems and methods that may allow for customization of the medical devices (additive manufacturing may also be described as three-dimensional (3D) printing). By using an additive manufacturing process/system to manufacture the medical devices described herein, a wider variety of hardness levels can be achieved compared to existing techniques to produce catheters, catheter components, or implantable devices. Further, the additive manufacturing process allows for various tooling and processes to design and develop specific medical device features that may be difficult to otherwise make. For example, the processes/systems may be similar to a polymer printer and polymer lathe that can be uses to create and refine any particular medical device. As such, new designs and new dimensions may be created in an efficient way. For example; the systems and techniques described herein may allow for integrating features quickly, iterating designs, and designing new geometries and features in a more specific manner. Specifically, the shape and/or size of the medical device or features disposed thereon may be readily manufactured to the operator's specifications. Therefore, the unique characteristics of a patient's vasculature may be accounted for when designing and manufacturing the medical device.

Although the medical devices described herein can be manufactured using additive manufacturing, it should be understood that other manufacturing techniques can also be used (e.g., reflow, molds, etc.) alone or in combination with each other and/or additive manufacturing to create the medical devices described herein. For example, in one embodiment, a groove for a pull wire may be formed in a medical device as described herein, followed by reflowing material over the medical device after placement of a pull wire to complete the manufacturing process.

In a first aspect, one or more embodiments of a medical device in the form a catheter/lead as described herein may include: an elongated catheter body extending along a catheter axis; and a pull wire extending along catheter body, the pull wire located within the catheter body and extending to an anchor at a distal end of the pull wire, wherein a location of the pull wire relative to the catheter axis changes when moving along the elongated catheter body from a proximal end of the catheter body towards the distal end of the catheter body, wherein the pull wire is configured to deflect the catheter body in two or more planes when pulled in a direction away from the anchor.

In one or more embodiments of a medical device according to the first aspect, the location of the pull wire moves radially towards and/or away from the central axis when moving along the elongated catheter body.

In one or more embodiments of a medical device according to the first aspect, the location of the pull wire moves around at least a portion of the circumference of the catheter body when moving along the elongated catheter body.

In one or more embodiments of a medical device according to the first aspect, the pull wire comprises the only pull wire located in the catheter body.

In one or more embodiments of a medical device according to the first aspect, relative to the catheter axis and over a selected portion of a length of the catheter body extending from a start location to a finish location, the pull wire moves, from the start location to the finish location over the selected portion, over an arc of 1 degree or more, 2 degrees or more, 3 degrees or more, 4 degrees or more, or 5 degrees or more at a low end and X+(n*360) degrees or less at an upper end, where X is 360 degrees or less, 330 degrees or less, 300 degrees or less, 270 degrees or less, 240 degrees or less, 210 degrees or less, 180 degrees or less, 150 degrees or less, 135 degrees or less, 120 degrees or less, 90 degrees or less, 75 degrees or less, 60 degrees or less, 45 degrees or less, 30 degrees or less, 15 degrees or less, 10 degrees or less, or 5 degrees or less and n is 0, 1, 2 or more. In one or more embodiments, the selected portion comprises 50% or less, 40% or less, 30% or less, 20% or less, or 10% or less of a total length of the catheter body as measured from the proximal end to the distal end.

In one or more embodiments of a medical device according to the first aspect: at a first location along a length of the catheter body, the pull wire is located at a first clock position within the catheter relative to the catheter axis; at a second location distal from the first location, the pull wire is located at a second clock position that is offset from the first clock position within the catheter relative to the catheter axis; and at a third location distal from the second location, the pull wire is located at a third clock position that is offset from the second clock position within the catheter relative to the catheter axis. In one or more embodiments, a first rate of change in clock position between the first clock position and the second clock position is different from a second rate of change in clock position between the second clock position and the third clock position, and optionally, wherein a difference between the first rate of change and the second rate of change is 1 degree or more, 2 degrees or more, 3 degrees or more, 4 degrees or more, or 5 degrees or more at a low end and 90 degrees or less, 75 degrees or less, 60 degrees or less, 45 degrees or less, 30 degrees or less, 15 degrees or less, 10 degrees or less, or 5 degrees or less.

In one or more embodiments of a medical device according to the first aspect in which the location of the pull wire moves radially towards and/or away from the central axis when moving along the elongated catheter body: at a first location along a length of the catheter body, the pull wire is located at a first radial position within the catheter relative to the catheter axis; at a second location distal from the first location, the pull wire is located at a second radial position within the catheter relative to the catheter axis that is different than the first radial position; and at a third location distal from the second location, the pull wire is located at a third radial position within the catheter relative to the catheter axis that is different than the second radial position. In one or more embodiments, a first rate of change in radial position between the first radial position and the second radial position is different from a second rate of change in radial position between the second radial position and the third radial position.

In a second aspect, one or more embodiments of a medical device in the form a catheter/lead as described herein includes: an elongated catheter body extending along a catheter axis from a proximal end to a distal end; and a pull wire extending through the catheter body, the pull wire located within the catheter body and extending to an anchor at a distal end of the pull wire, wherein the anchor is fixed in position relative to the catheter body, and wherein the pull wire extends proximally from the anchor towards the proximal end of the catheter body; wherein the catheter body comprises a first portion and a second portion, wherein the first portion and the second portion occupy different portions of a length of the catheter body; wherein the first portion of the catheter body is configured to form a curved first portion when the pull wire is placed in tension between the anchor and the proximal end of the catheter body, wherein the catheter axis in the curved first portion forms a curve when projected onto the X-Y plane along a Z axis of a three dimensional Cartesian coordinate system; and wherein the second portion of the catheter body is configured to form a curved second portion when the pull wire is placed in tension between the anchor and the proximal end of the catheter body, wherein the catheter axis in the curved second portion forms a curve when projected onto the X-Z plane along a Y axis of the three dimensional Cartesian coordinate system.

In one or more embodiments of a medical device according to the second aspect, a radius of curvature of the curve located in an X-Y plane is different than a radius of curvature of the curve located in the X-Z plane.

In one or more embodiments of a medical device according to the second aspect, the first portion is configured to form the first curved portion before the second portion forms the second curved portion when the pull wire is placed in tension between the anchor and the proximal end of the catheter body. In one or more embodiments, a first volume of material forming the first portion of the catheter body is less than a second volume of material forming the second portion of the catheter body. In one or more embodiments, the first portion of the catheter body comprises a composite EI value that is less than a composite EI value of the second portion of the catheter body, wherein, optionally, the composite EI value of the first portion is 90% or less, 75% or less, 50% or less, 40% or less, 30% or less, 20% or less, or even 10% or less of the composite EI value of the second portion of the catheter body.

In one or more embodiments of a medical device according to the second aspect, the catheter body comprises a third portion, wherein the third portion occupies a different portion of the length of the catheter body than the first portion and the second portion; wherein the third portion of the catheter body is configured to form a curved third portion when the pull wire is placed in tension between the anchor and the proximal end of the catheter body, wherein the catheter axis in the curved third portion forms a curve when projected onto the Y-Z plane along an X axis of the three dimensional Cartesian coordinate system. In one or more embodiments, a radius of curvature of the curve located in an X-Z plane is different than a radius of curvature of the curve located in the X-Y plane and also different than a radius of curvature of the curve located in the Y-Z plane. In one or more embodiments, the third portion is configured to form the third curved portion after the first portion forms the curved first portion and the second portion forms the second curved portion when the pull wire is placed in tension between the anchor and the proximal end of the catheter body. In one or more embodiments, a third volume of material forming the third portion of the catheter body is less than the first volume of material forming the first portion of the catheter body. In one or more embodiments, the third portion of the catheter body comprises a composite EI value that is less than a composite EI value of the first portion of the catheter body, wherein, optionally, the composite EI value of the third portion is 90% or less, 75% or less, 50% or less, 40% or less, 30% or less, 20% or less, or even 10% or less of the composite EI value of the first portion of the catheter body.

In one or more embodiments of a medical device according to the second aspect, the catheter body comprises an intermediate portion located between the first portion and the second portion, wherein the intermediate portion is not configured to form a curved intermediate portion when the pull wire is placed in tension between the anchor and the proximal end of the catheter body.

In one or more embodiments of a medical device according to the second aspect, the first portion of the catheter body comprises a core formed of a core material and a jacket surrounding the core, wherein the jacket is formed of a jacket material, wherein the jacket material comprises a modulus of elasticity that is different than a modulus of elasticity of the core material, and wherein the jacket material is non-uniformly distributed about the catheter axis. In one or more embodiments, the second portion of the catheter body comprises a core formed of the core material and a jacket surrounding the core, wherein the jacket of the second portion is formed of the jacket material, wherein the jacket material comprises a modulus of elasticity that is different than a modulus of elasticity of the core material, and wherein the jacket material is non-uniformly distributed about the catheter axis. In one or more embodiments, the modulus of elasticity of the jacket material is less than the modulus of elasticity of the core material.

In one or more embodiments of a medical device according to the second aspect, the pull wire comprises the only pull wire located in the catheter body.

In one or more embodiments of a medical device according to the second aspect, the pull wire moves around at least a portion of the circumference of the catheter body when moving along the elongated catheter body from the proximal end of the catheter body towards the distal end of the catheter body. In one or more embodiments, the pull wire moves, relative to the catheter axis and over a selected portion of a length of the catheter body extending from a start location to a finish location, the pull wire moves, from the start location to the finish location over the selected portion, over an arc of 1 degree or more, 2 degrees or more, 3 degrees or more, 4 degrees or more, or 5 degrees or more at a low end and X+(n*360) degrees or less at an upper end, where X is 360 degrees or less, 330 degrees or less, 300 degrees or less, 270 degrees or less, 240 degrees or less, 210 degrees or less, 180 degrees or less, 150 degrees or less, 135 degrees or less, 120 degrees or less, 90 degrees or less, 75 degrees or less, 60 degrees or less, 45 degrees or less, 30 degrees or less, 15 degrees or less, 10 degrees or less, or 5 degrees or less and n is 0, 1, 2 or more. In one or more embodiments, the selected portion comprises 50% or less, 40% or less, 30% or less, 20% or less, or 10% or less of a total length of the catheter body as measured from the proximal end to the distal end. In one or more embodiments of a medical device in which the pull wire moves around at least a portion of the circumference of the catheter body: at a first location along a length of the catheter body, the pull wire is located at a first clock position within the catheter relative to the catheter axis; at a second location distal from the first location, the pull wire is located at a second clock position that is offset from the first clock position within the catheter relative to the catheter axis; and at a third location distal from the second location, the pull wire is located at a third clock position that is offset from the second clock position within the catheter relative to the catheter axis. In one or more embodiments, a first rate of change in clock position between the first clock position and the second clock position is different from a second rate of change in clock position between the second clock position and the third clock position, and optionally, wherein a difference between the first rate of change and the second rate of change is, relative to the catheter axis, 1 degree or more, 2 degrees or more, 3 degrees or more, 4 degrees or more, or 5 degrees or more at a low end and 90 degrees or less, 75 degrees or less, 60 degrees or less, 45 degrees or less, 30 degrees or less, 15 degrees or less, 10 degrees or less, or 5 degrees or less.

In one or more embodiments of any medical device described herein, the pull wire is located within a pull wire lumen provided in the catheter body.

In a third aspect, one or more embodiments of an additive manufacturing system as described herein includes:
  a. a heating cartridge extending from a proximal side to a distal side and comprising a substrate inlet port at the proximal side and a substrate outlet port at the distal side, the heating cartridge defining an interior volume and a substrate channel extending through the interior volume from the proximal side to the distal side, wherein the heating cartridge defines a first filament port in fluid communication with the interior volume to receive the first filament;
  b. a heating element thermally coupled to the heating cartridge to heat the interior volume;
  c. a filament handling system comprising one or more motors to feed at least a first filament through the first filament port into the interior volume;
  d. a pull wire handling system configured to deliver a pull wire to a pull wire notch in the substrate channel of the heating cartridge;
  e. a substrate handling system comprising:
    i. a head stock comprising a distal clamp to secure a distal portion of an elongate substrate, wherein the substrate is positioned to pass through the substrate channel along a longitudinal axis when secured by the head stock; and ii. one or more motors to translate or rotate the substrate and the heating cartridge relative to each other when the substrate is secured by the headstock, wherein the pull wire translates or rotates in synchrony with the substrate;

f. a controller operably coupled to the heating element, one or more motors of the filament handling system, and one or more motors of the substrate handling system, the controller configured to:

i. activate the heating element to melt any portion of the first filament in the interior volume;

ii. control the one or more motors of the filament handling system to selectively control the feeding of the first filament into the interior volume; and iii. control one or more motors of the substrate handling system to move one or both of the substrate and the heating cartridge relative to one another in a longitudinal direction while rotating one or both of the substrate and the heating cartridge about the longitudinal direction to form an elongate catheter jacket around the substrate which includes a pull wire wrapped around substrate, wherein the catheter jacket comprises material from the first filament.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWING

FIG. 6 is a conceptual diagram of an illustrative catheter as described herein including a pull wire having a circumferential position that moves along the length of the catheter body.

FIGS. 7-11 are cross-sectional views of the illustrative catheter of FIG. 6 taken in planes transverse to the catheter axis to illustrate the changing location of the pull wire within the catheter body when moving along the length of the catheter, with each cross-sectional view being taken along the section line (e.g., 7-7, 8-8, etc.) corresponding to the figure number in FIG. 6.

FIG. 12A is a conceptual diagram of another illustrative catheter as described herein including a pull wire having a radial position that changes along the length of the catheter body.

FIGS. 12B-12D are cross-sectional views of the illustrative catheter of FIG. 12A taken in planes transverse to the catheter axis to illustrate the changing radial position of the pull wire within the catheter body when moving along the length of the catheter.

FIG. 13A is a conceptual diagram of another illustrative catheter as described herein in which both the circumferential and radial positions of a pull wire change over a selected portion of the length of the catheter body.

FIGS. 13B and 13C are cross-sectional views of the illustrative catheter of FIG. 13A taken in planes transverse to the catheter axis (along, respectively, lines 13B-13B and 13C-13C in FIG. 13A) to illustrate the changes in both circumferential and radial positions of the pull wire within the catheter body.

FIG. 14 is a perspective view of another illustrative embodiment of a catheter as described herein after a pull wire located within the catheter body is placed in tension.

FIG. 15 is a schematic diagram of the catheter of FIG. 14 before the catheter is placed in tension using the pull wire.

FIG. 15A is an enlarged cross-sectional view of the catheter of FIG. 15 taken along line 15A-15A in FIG. 15.

FIG. 23 depicts another illustrative embodiment of a catheter as described herein in a relaxed state.

FIG. 24 depicts the catheter of FIG. 23 after a pull wire extending through the catheter body is pulled to place the catheter body in tension as described herein.

FIG. 25 is a cross-sectional view of the catheter of FIG. 23 taken along line 25-25 in FIG. 23.

FIG. 26 depicts another illustrative embodiment of a catheter as described herein in a relaxed state.

FIG. 27 depicts the catheter of FIG. 26 after a pull wire extending through the catheter body is pulled to place the catheter body in tension as described herein.

FIG. 28 is a cross-sectional view of the catheter of FIG. 26 taken along line 28-28 in FIG. 26.

FIG. 29 is a cross-sectional view of the catheter of FIG. 26 taken along line 29-29 in FIG. 26.

FIG. 30 is a cross-sectional view of another illustrative embodiment of a catheter as described herein depicting a core, a jacket, and a pull wire of the catheter, the cross-sectional view taken along a plane containing the catheter axis 1026 and the pull wire 1070.

FIG. 31 is a cross-sectional view of the catheter of FIG. 30 taken along line 31-31 in FIG. 30.

FIG. 32 is a cross-sectional view of another illustrative embodiment of a catheter as described herein depicting a core, a jacket, and a pull wire of the catheter taken along a plane containing the catheter axis 1126 and the pull wire 1170

FIG. 33 is a cross-sectional view of the catheter of FIG. 32 taken along line 33-33 in FIG. 32.

FIGS. 34-38 depict one illustrative embodiment of a catheter as described herein depicting deflection of the catheter in three dimensions as a pull wire located within the catheter body is pulled relative to an anchor proximate the distal end of the depicted catheter.

DETAILED DESCRIPTION

Figure 1:
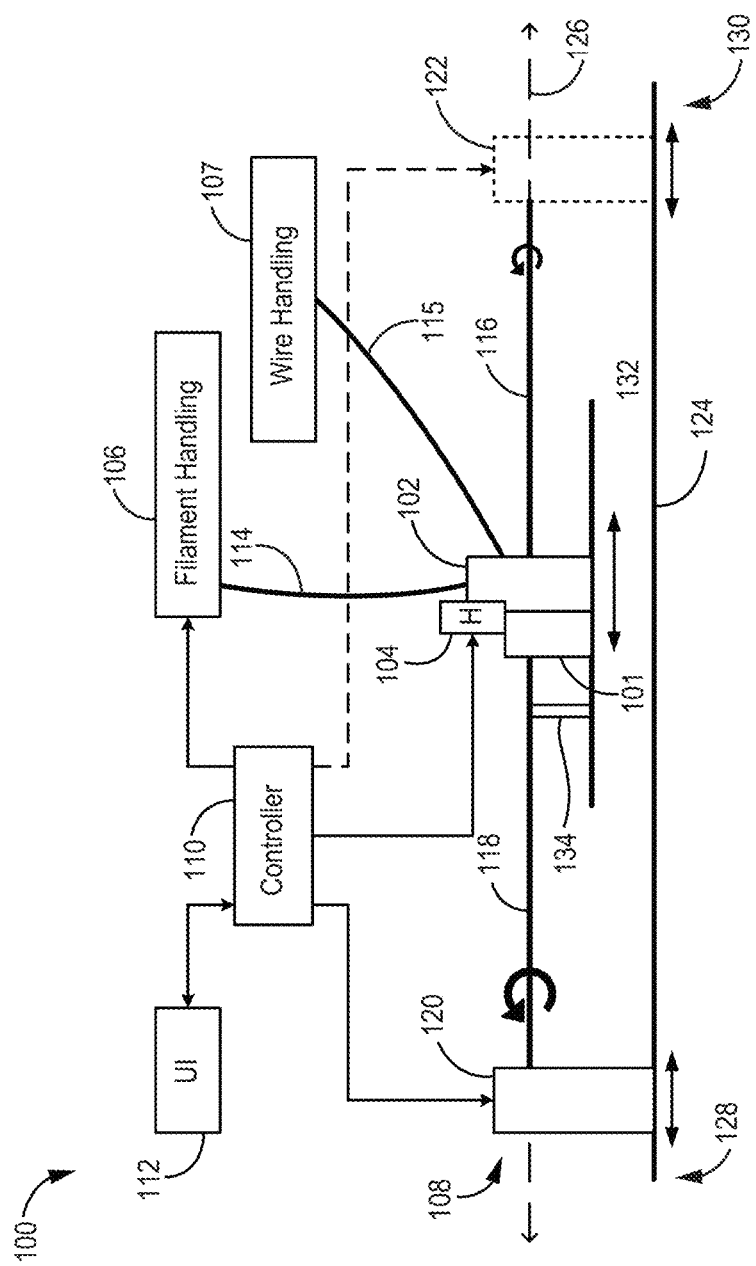
FIG. 1 is a conceptual diagram of an illustrative additive manufacturing system according to the present disclosure.

The present disclosure generally relates to medical devices (such as catheters and leads—both of which are commonly referred to herein as catheters) that provide for selected curve deflection in multiple planes such that three-dimensional shapes can be formed in the catheters by placing pull wires located in the catheters in tension as described herein, as well as methods of manufacturing and using the medical devices.

As used herein, the term "or" refers to an inclusive definition, for example, to mean "and/or" unless its context of usage clearly dictates otherwise. The term "and/or" refers to one or all of the listed elements or a combination of at least two of the listed elements.

As used herein, the phrases "at least one of" and "one or more of" followed by a list of elements refers to one or more of any of the elements listed or any combination of one or more of the elements listed.

As used herein, the terms "coupled" or "connected" refer to at least two elements being attached to each other either directly or indirectly. An indirect coupling may include one or more other elements between the at least two elements being attached. Either term may be modified by "operatively" and "operably," which may be used interchangeably, to describe that the coupling or connection is configured to allow the components to interact to carry out described or otherwise known functionality. For example, a controller may be operably coupled to a resistive heating element to allow the controller to provide an electrical current to the heating element.

As used herein, any term related to position or orientation, such as "proximal," "distal," "end," "outer," "inner," and the like, refers to a relative position and does not limit the absolute orientation of an embodiment unless its context of usage clearly dictates otherwise.

All scientific and technical terms used herein have meanings commonly used in the art unless otherwise specified. The definitions provided herein are to facilitate understanding of certain terms used frequently herein and are not meant to limit the scope of the present disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows one example of an additive manufacturing system 100 according to the present disclosure. The system 100 may be configured and used to produce a catheter, catheter component, lead, or subassembly. The system 100 may use or include consumable filament materials or pellet form resins having a wide variety of hardness levels. The system 100 may be configured to operate a wide variety of process conditions to produce catheters, catheter components, leads, or subassemblies using filaments or pellet form resins of various hardness levels. In general, the system 100 defines a distal region 128, or distal end, and a proximal region 130, or proximal end. The system 100 may include a platform 124 including a rigid frame to support one or more components of the system.

Further components of the system 100 may be shown as described in U.S. Pat. App. No. 62/927,092, entitled "ADDITIVE MANUFACTURING FOR MEDICAL DEVICES" and, further, methods of manufacturing catheters as described herein may be further described in U.S. Patent Application No. 63/059,867, entitled "SYSTEMS AND METHODS FOR MANUFACTURING 3D PRINTED MEDICAL DEVICES, both of which are herein incorporated by reference. For example, as shown in the illustrated embodiment, the system 100 may include one or more components, such as a heating cartridge 102, a heating element 104, a filament handling system 106, an optional wire handling system 107, a substrate handling system 108, a controller 110, and a user interface 112. The filament handling system 106 may be operably coupled to the heating cartridge 102. The filament handling system 106 may provide one or more filaments 114 to the heating cartridge 102. The optional wire handling system 107 may be used to provide one or more wires 115 to the heating cartridge 102. The heating element 104 may be operably coupled, or thermally coupled, to the heating cartridge 102. The heating element 104 may provide heat to melt filament material in the heating cartridge 102 from the one or more filaments 114 provided by the filament handling system 106. The optional wires 115 may not be melted by the heating cartridge 102. The substrate handling system 108 may be operably coupled to the heating cartridge 102. The substrate handling system 108 may provide a substrate 116 that extends through the heating cartridge. Melted filament material located in the heating cartridge 102 may be applied to the substrate 116. The substrate 116 or the heating cartridge 102 may be translated or rotated relative to one another by the substrate handling system 108. The substrate handling system 108 may be used to move the substrate 116 or the heating cartridge 102 relative to one another to cover the substrate 116 with the melted filament material to form a jacket 118. The optional wires 115 may be incorporated into the jacket 118 (e.g., molded into, bedded within, etc.).

The substrate 116 may also be described as a mandrel or rod. The jacket 118 may be formed or deposited around the substrate 116. In some embodiments, the jacket 118 may be formed concentrically around the substrate 116. In one example, the jacket 118 is formed concentrically and centered around the substrate 116.

When the system 100 is used to make a catheter or catheter component, the jacket 118 may be described as a catheter jacket. Some or all of the substrate 116 may be removed or separated from the jacket 118 and the remaining structure coupled to the jacket may form the catheter or catheter component, such as a sheath. One example of a catheter that may be formed by the system 100 is shown in FIG. 6.

The substrate 116 may be formed of any suitable material capable of allowing melted filament material to be formed thereon. In some embodiments, the substrate 116 is formed of a material that melts at a higher temperature than any of the filaments 114. One example of a material that may be used to form the substrate 116 includes stainless steel.

The controller 110 may be operably coupled to one or more of the heating element 104, the filament handling system 106, the substrate handling system 108, and the user interface 112. The controller 110 may activate, or initiate or otherwise "turn on," the heating element 104 to provide heat to the heating cartridge 102 to melt the filament material located therein. Further, the controller 110 may control or command one or more motors or actuators of various portions of the system 100. Furthermore, the controller 110 may control one or more motors or actuators the filament handling system 106 to provide one or more filaments 114. Further, the controller 110 may control one or more motors or actuators of the substrate handling system 108 to move one or both of the heating cartridge 102 or the substrate 116 relative to one another. Further still, the controller 110 may send or receive data to the user interface 112, for example, to display information or to receive user commands. Control of the components operably coupled to the controller 110 may be determined based on user commands received by the user interface 112. In some embodiments, the user commands may be provided in the form of a machine-readable code or coding language.

Any suitable implementation may be used to provide the substrate handling system 108. In some embodiments, the substrate handling system 108 may include one or more of a head stock 120, an optional tail stock 122, and one or more motors coupled to or included in the head stock or tail stock. One or both of the head stock 120 and the tail stock 122 may be coupled to the platform 124. A stock may be defined as a structure that holds or secures the substrate 116 during formation of the jacket 118. The head stock 120 is defined as the stock closest to the end of the substrate 116 where formation of the jacket 118 begins in the formation process. In the illustrated embodiment, the jacket 118 is shown proximal to the head stock 120 and distal to the heating cartridge 102.

When the substrate 116 is secured by one or both stocks 120, 122, the substrate is generally positioned to pass through a substrate channel defined by the heating cartridge 102. One or both stocks 120, 122 may include a clamp or other securing mechanism to selectively hold the substrate 116. Such a clamp may be operably coupled to a substrate motor. In some embodiments, the substrate motor may be used to control opening and closing of the clamp. In some embodiments, the substrate motor may be used to rotate the substrate 116 in a clockwise or counterclockwise direction about a longitudinal axis 126. A translation motor may be operably coupled between a stock 120, 122 and the platform 124. In some embodiments, the translation motor may be used to translate the stock 120, 122 in a longitudinal direction along the longitudinal axis 126. In some embodiments, the translation motor also may be used to translate the stock 120, 122 in a lateral direction different than the longitudinal axis 126. The lateral direction may be oriented substantially orthogonal, or perpendicular, to the longitudinal axis 126.

In some embodiments, the substrate handling system 108 may be configured to move the head stock 120 at least in a longitudinal direction (for example, parallel to the longitudinal axis 126) relative to the platform 124. The substrate 116 may be fed through the substrate channel of the heating cartridge 102 by movement of the head stock 120 relative to the platform 124. A distal portion of the substrate 116 may be clamped into the head stock 120. The head stock 120 may be positioned close to the heating cartridge 102 at the beginning of the jacket formation process. The head stock 120 may move distally away from the heating cartridge 102, for example in a direction parallel to the longitudinal axis 126. In other words, the head stock 120 may move toward the distal region 128 of the system 100 while pulling the secured substrate 116 through the heating cartridge 102. As the substrate 116 passes through the heating cartridge 102, melted filament material from the filament 114 may be formed or deposited onto the substrate 116 to form the jacket 118. The heating cartridge 102 may be stationary relative to the platform 124. In some embodiments, the tail stock 122 may be omitted.

In some embodiments, the substrate handling system 108 may be configured to move the heating cartridge 102 at least in a longitudinal direction (along the longitudinal axis 126) relative to the platform 124. The substrate 116 may be fed through the substrate channel of the heating cartridge 102. A distal portion of the substrate 116 may be clamped into the head stock 120. A proximal portion of the substrate 116 may be clamped into the tail stock 122. In one example, the heating cartridge 102 may be positioned relatively close to the head stock 120 at the beginning of the jacket formation process. The heating cartridge 102 may move proximally away from the head stock 120. The heating cartridge 102 may move toward the proximal region 130 of the system 100. As the heating cartridge 102 passes over the substrate 116, melted filament material may be deposited onto the substrate 116 to form a jacket. The head stock 120 and the tail stock 122 may be stationary relative to the platform 124. In another example, the heating cartridge 102 may start near the tail stock 122 and move toward the distal region 128.

One or more motors of the substrate handling system 108 may be used to rotate one or both of the substrate 116 and the heating cartridge 102 relative to one another. In some embodiments, only the substrate 116 may be rotated about the longitudinal axis 126. In some embodiments, only the heating cartridge 102 may be rotated about the longitudinal axis 126. In some embodiments, both the substrate 116 and the heating cartridge 102 may be rotated about the longitudinal axis 126.

The heating cartridge 102 may be part of a subassembly 132. The subassembly 132 may be coupled to the platform 124. In some embodiments, one or more motors of the substrate handling system 108 may be coupled between subassembly 132 and the platform 124 to translate or rotate the subassembly 132, including the heating cartridge 102, relative to the platform 124 or the substrate 116. In some embodiments, one or more motors of the substrate handling system 108 may be coupled between a frame of the subassembly 132 and the heating cartridge 102 to translate or rotate the heating cartridge relative to the platform 124.

In some embodiments, the substrate 116 may be rotated about the longitudinal axis 126 relative to the heating cartridge 102 to facilitate forming certain structures of the jacket. In one example, the substrate 116 may be rotated by one or both of the head stock 120 and the tail stock 122 of the substrate handling system 108. In another example, the heating cartridge 102 or subassembly 132 may be rotated by the substrate handling system 108.

The system 100 may include one or more concentricity guides 134. The concentricity guide 134 may facilitate adjustments to the concentricity of the jacket around the substrate 116 before or after the substrate passes through the heating cartridge 102. The concentricity guide 134 may be longitudinally spaced from the heating cartridge 102. In some embodiments, the spacing may be greater than or equal to 1, 2, 3, 4, or 5 cm. The spacing may be sufficient to allow the jacket 118 to cool down and no longer be deformable. In some embodiments, one or more concentricity guides 134 may be positioned distal to the heating cartridge 102 and to engage the jacket 118. In some embodiments, one or more concentricity guides 134 may be positioned proximal to the heating cartridge 102 to engage the substrate 116. The concentricity guide 134 may mitigate drooping of the substrate 116 and may mitigate susceptibility to eccentricity in the alignment of the stock 120, 122 and the heating cartridge 102.

Any suitable implementation may be used to provide the filament handling system 106. One or more filaments 114 may be loaded into the filament handling system 106. For example, filaments 114 may be provided in the form of wound coils. Filaments 114 may be fed to the heating cartridge 102 by the filament handling system 106. In some embodiments, the filament handling system 106 may include one, two, or more pinch rollers to engage the one or more filaments 114. In some embodiments, the filament handling system 106 may include one or more motors. The one or more motors may be coupled to the one or more pinch rollers to control rotation of the pinch rollers. The force exerted by the motors onto the pinch rollers and thus onto the one or more filaments 114 may be controlled by the controller 110.

In some embodiments, the filament handling system 106 may be configured to feed the filaments 114 including at least a first filament and a second filament. The jacket 118 may be formed from the material of one or both of the filaments 114. The filament handling system 106 may be capable of selectively feeding the first filament and the second filament. For example, one motor may feed the first filament and another motor may feed the second filament. Each of the motors may be independently controlled by the controller 110. Selective, or independent, control of the feeds may allow for the same or different feed forces to be applied to each of the filaments 114.

The filaments 114 may be made of any suitable material, such as polyethylene, PEBAX elastomer (commercially available from Arkema S.A. of Colombes, France), nylon 12, polyurethane, polyester, liquid silicone rubber (LSR), or PTFE.

The filaments 114 may have any suitable Shore durometer. In some embodiments, the filaments 114 may have, or define, a Shore durometer suitable for use in a catheter. In some embodiments, the filaments 114 have a Shore durometer of at least 25A and up to 90A. In some embodiments, the filaments 114 have a Shore durometer of at least 25D and up to 80D.

In some embodiments, the filament handling system 106 may provide a soft filament as one of the filaments 114. In some embodiments, a soft filament may have a Shore durometer less than or equal to 90A, 80A, 70A, 80D, 72D, 70D, 60D, 50D, 40D, or 35D.

In some embodiments, the filament handling system 106 may provide a hard filament and a soft filament having a Shore durometer less than the soft filament. In some embodiments, the soft filament has a Shore durometer that is 10D, 20D, 30D, 35D, or 40D less than a Shore durometer of the hard filament.

The system 100 may be configured to provide a jacket 118 between the Shore durometers of a hard filament and a soft filament. In some embodiments, the filament handling system 106 may provide a hard filament having a Shore durometer equal to 72D and a soft filament having a Shore durometer equal to 35D. The system 100 may be capable of providing a jacket 118 having a Shore durometer that is equal to or greater than 35D and less than or equal to 72D.

The system 100 may be configured to provide a jacket 118 having, or defining, segments with different Shore durometers. In some embodiments, the system 100 may be capable of providing a jacket 118 having one or more of a 35D segment, a 40D segment, 55D segment, and a 72D segment.

The filaments 114 may have any suitable width or diameter. In some embodiments, the filaments 114 have a width or diameter of 1.75 mm. In some embodiments, the filaments 114 have a width or diameter of less than or equal to 1.75, 1.5, 1.25, 1, 0.75, or 0.5 mm.

Segments may have uniform or non-uniform Shore durometers. The system 100 may be configured to provide jacket 118 having one or more segments with non-uniform Shore durometers. In some embodiments, the jacket 118 may include continuous transitions between at least two different Shore durometers, for example, as shown in FIG. 6.

The controller 110 may be configured to change a feeding force applied to one or more of the filaments 114 to change a ratio of material in the jacket over a longitudinal distance. By varying the feeding force, the system 100 may provide different Shore durometer segments in a jacket 118, whether uniform or non-uniform. In one example, sharp transitions between uniform segments may be provided by stopping or slowing longitudinal movement while continuously, or discretely with a large step, changing the feeding force of one filament relative to another filament of the substrate 116 relative to the heating cartridge 102. In another example, gradual transitions between segments may be provided by continuously, or discretely with small steps, changing the feeding force of one filament relative to another filament while longitudinally moving the substrate 116 relative to the heating cartridge 102.

The one or more wires 115 provided by the wire handling system 107 may be introduced in any suitable manner. In some embodiments, the wires 115 may be attached to the substrate 116 and pulled by movement of the substrate. One example of a wire is a pull wire that may be used to steer the catheter produced by the system 100. In some embodiments, a particularly shaped heating cartridge may be used to accommodate one or more wires 115.

Any suitable type of heating element 104 may be used. In some embodiments, the heating element 104 may be a resistive-type heating element, which may provide heat in response to an electrical current. Other types of heating elements that may be used for the heating element 104 include a radio frequency (RF) or ultrasonic-type heating element. The heating element 104 may be capable of providing heat sufficient to melt the filaments 114. In some embodiments, the heating element 104 may heat the filaments 114 to greater than or equal to 235, 240, 250, or 260 degrees Celsius. In general, the one or more heating elements 104 may be used to heat the filaments 114 to any suitable melting temperature known to one of ordinary skill in the art having the benefit of this disclosure.

Figure 2:
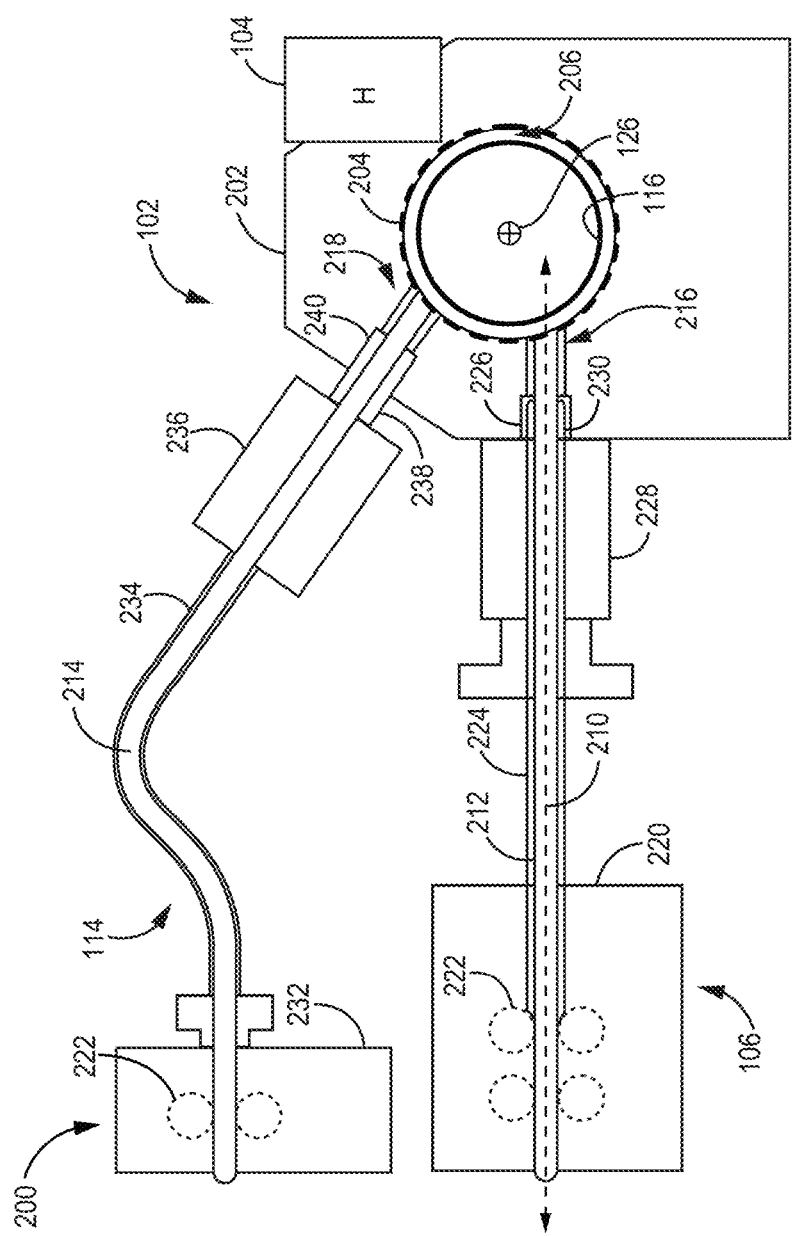
FIG. 2 is a conceptual diagram of an illustrative additive manufacturing apparatus for use with, for example, the additive manufacturing system of FIG. 1.

FIG. 2 shows one example of an additive manufacturing apparatus 200 of the additive manufacturing system 100 in an end view along the longitudinal axis 126, which is illustrated as a circle and cross. More detail of some components of the additive manufacturing system 100 are shown, such as the heating cartridge 102 and the filament handling system 106.

The heating cartridge 102 may include a heating block 202 at least partially defining an interior volume 204. The interior volume 204 may be heated by the heating element 104. The heating element 104 may be thermally coupled to the heating block 202 to melt filament material in the interior volume 204. In general, the system 100 may be configured to melt any portion of the filaments 114 in the interior volume 204. The heating element 104 may be disposed in an exposed or exterior volume defined in the heating block 202. The heating element 104 may be positioned proximate to or adjacent to the interior volume 204. In some embodiments, one, two, three, or more heating elements 104 may be thermally coupled to the heating block 202.

The heating block 202 may allow the substrate 116, which may be an elongate substrate or member, to pass through the heating block. The substrate 116 may be able to extend, or pass, through the interior volume 204. The substrate channel 206 defined by the heating cartridge 102 may extend through the interior volume 204. The substrate channel 206 may extend in a same or similar direction as the substrate 116. The substrate channel 206 may extend along the longitudinal axis 126.

A width or diameter of the interior volume 204 is larger than a width or diameter of the substrate 116. The width or diameter of the interior volume 204 or the substrate 116 is defined in a lateral direction, which may be orthogonal to the longitudinal axis 126. In one example, the lateral direction may be defined along a lateral axis 210. In some embodiments, the clearance between the substrate 116 and interior volume 204 is relatively small to facilitate changes in composition of filament material used to form the jacket 118 (FIG. 1) around the substrate 116.

The portion of the interior volume 204 around the substrate 116 may receive a flow of melted filament material from the filaments 114. When more than one filament material is provided to the interior volume 204, the filament materials may flow and blend, or mix, around the substrate 116.

In the illustrated embodiment, the filaments 114 includes a first filament 212 and a second filament 214. The first filament 212 may be provided into the interior volume 204 through a first filament port 216 at least partially defined by the heating block 202. The second filament 214 may be provided into the interior volume 204 through a second filament port 218 at least partially defined by the heating block 202. Each filament port 216, 218 may be at least partially defined by the heating block 202. Each filament port 216, 218 may be in fluid communication with the interior volume 204.

The filaments 114 may be delivered to the interior volume 204 in the same or different manners. In the illustrated embodiment, the first filament 212 is delivered to the interior volume 204 in a different manner than the second filament 214.

The filament handling system 106 may include a first handling subassembly 220. The first handling subassembly 220 may deliver the first filament 212 to the interior volume 204. The first handling subassembly 220 may include one or more pinch rollers 222. Each of the one or more pinch rollers 222 may be operably coupled to a motor. Any suitable number of pinch rollers 222 may be used. As illustrated, the first handling subassembly 220 may include two sets of pinch rollers 222. Pinch rollers 222 may be used to apply a motive force to the first filament 212 to move the first filament, for example, toward the interior volume 204.

The heating cartridge 102 may include a first guide sheath 224. The first guide sheath 224 may extend between the filament handling system 106 and the interior volume 204. The first guide sheath 224 may be coupled to the heating block 202. The first guide sheath 224 may extend into the first filament port 216 from an exterior of the heating block 202. The first guide sheath 224 may define a lumen in fluid communication with the interior volume 204. An inner width or diameter of the lumen may be defined to be greater than a width or diameter of the first filament 212. The first filament 212 may extend through the first guide sheath 224 from the pinch rollers 222 of the first handling subassembly 220 to the first filament port 216 and extend distally past the first guide sheath 224 into the interior volume 204.

As used herein with respect to the filaments 114, the term "distal" refers to a direction closer to the interior volume 204 and the term "proximal" refers to a direction closer to the filament handling system 106.

In some embodiments, a proximal end of the first guide sheath 224 may terminate proximate to one of the pinch rollers 222. A distal end of the first guide sheath 224 may terminate at a shoulder 226 defined by the first filament port 216. A distal portion or distal end of the first guide sheath 224 may be positioned proximate to or adjacent to the interior volume 204.

The inner width or diameter of the lumen of the first guide sheath 224 may be defined to be substantially the same or equal to an inner width or diameter of the first filament port 216, such as a smallest inner width or diameter of the first filament port. In other words, an inner surface of the first guide sheath 224 may be flush with an inner surface of the first filament port 216.

In some embodiments, the heating cartridge 102 may include a support element 228. The support element 228 may be coupled to the first guide sheath 224. The first guide sheath 224 may extend through a lumen defined by the support element 228. The support element 228 may be proximate to the heating block 202. In the illustrated embodiment, the support element 228 is coupled to the heating block 202. The support element 228 may include a coupling protrusion configured to be mechanically coupled to a coupling receptacle 230 defined by the first filament port 216. In some embodiments, the coupling receptacle 230 may define threads and the coupling protrusion of the support element 228 may define complementary threads.

The coupling receptacle 230 may terminate at the shoulder 226 of the first filament port 216. The coupling protrusion of the support element 228 may be designed to terminate at the shoulder 226. In some embodiments, a distal end of the support element 228 and the distal end of the first guide sheath 224 may engage the shoulder 226. In other embodiments, the distal end of the support element 228 may engage the shoulder 226 and the distal end of the first guide sheath 224 may engage a second shoulder (not shown) defined by the first filament port 216 distal to the shoulder 226.

When the first filament port 216 defines one shoulder, the first filament port 216 may define at least two different inner widths or diameters. The larger inner width or diameter may be sized to thread the support element 228 and the smaller inner width or diameter may be sized to match the inner width or diameter of the first guide sheath 224.

When the second filament port 218 defines two shoulders, the first filament port 216 may define at least three different inner widths or diameters. The largest inner width or diameter may be sized to thread the support element 228. The intermediate inner width or diameter may be sized to receive a distal portion of the first guide sheath 224. The smallest inner width or diameter may be sized to match the inner width or diameter of the first guide sheath 224.

The filament handling system 106 may include a second handling subassembly 232. The second handling subassembly 232 may deliver the second filament 214 to the interior volume 204. The second handling subassembly 232 may include one or more pinch rollers 222. Each of the one or more pinch rollers 222 may be operably coupled to a motor. Any suitable number of pinch rollers 222 may be used. As illustrated, the second handling subassembly 232 may include one set of pinch rollers 222. Pinch rollers 222 may be used to apply a motive force to the second filament 214.

The heating cartridge 102 may include one or more of a second guide sheath 234, a heat sink 236, and a heat break 238. The second guide sheath 234 may extend at least between the second handling subassembly 232 and the heat sink 236. The second guide sheath 234 may be coupled to the heat sink. The second guide sheath 234 may be coupled to the second handling subassembly 232. The heat sink 236 may be coupled to the heat break 238. The heat break 238 may be coupled to the heat block 202. The heat break 238 may extend into the second filament port 218 from an exterior of the heating block 202.

The second guide sheath 234 may define a lumen in fluid communication with the interior volume 204. The second filament 214 may extend through the second guide sheath 234 from the second handling subassembly 232 to the heat sink 236, through the heat sink 236, through the heat break, and through the second filament port 218. In some embodiments, the second guide sheath 234 may extend to the pinch rollers 22 in the second handling subassembly 232. In some embodiments, the second guide sheath 234 may extend at least partially into the heat sink 236.

The heat break 238 may be proximate to the heating block 202. The heat break 238 may be positioned between the heat sink 236 and the heating block 202. The heat break 238 may include a coupling protrusion configured to mechanically couple to a coupling receptacle 240 defined by the second filament port 218. In some embodiments, the coupling receptacle 240 may define threads and the coupling protrusion of the heat break 238 may define complementary threads. The second filament port 218 may include one or more shoulders such as those described with respect to the first filament port 216, except that the second filament port 218 may not be configured to receive the second guide sheath 234. The inner width or diameter of the support element 228 may be larger than the inner width or diameter of the heat break 238, for example, to accommodate the outer width or diameter of the first guide sheath 224. In other embodiments, the second filament port 218 may be configured to receive the second guide sheath 234 in a similar manner to the first filament port 216 receiving the first guide sheath 224.

Any suitable material may be used to make the guide sheaths 224, 234. In some embodiments, one or both guide sheaths 224, 234 may include a synthetic fluoropolymer. One or both guide sheaths 224, 234 may include polytetrafluoroethylene (PTFE). Another suitable material may include an ultra-high molecular weight polyethylene (UHMWPE).

Any suitable material may be used to make the support element 228. In some embodiments, the support element 228 may be a thermal insulator. The support element 228 may include a thermoplastic. The support element 228 may be made of a polyamide-imide, such as a TORLON polyamide-imide (commercially available from McMaster-Carr Supply Co. of Elmhurst, Illinois). Other suitable materials may include liquid-crystal polymer, polyaryletherketone (PAEK), polyphenylene sulfide, and polysulfone.

The support element 228 may provide mechanical support to the first guide sheath 224. The support element 228 may include a substantially rigid material. In some embodiments, the support element 228 include a material having a higher durometer than material used to make the first guide sheath 224.

Any suitable material may be used to make the heat sink 236. The heat sink 236 may include a high thermal conductivity material. In some embodiments, the heat sink 236 includes aluminum.

Any suitable material may be used to make the heat break 238. The heat break 238 may include a low thermal conductivity material. In some embodiments, the heat break 238 includes titanium. The heat break 238 may include a necked portion to reduce the amount of material between a proximal portion and a distal portion of the heat break. The necked portion may facilitate a reduced thermal conductivity between the proximal portion and the distal portion of the heat break 238.

In general, use of the apparatus 200 may facilitate using softer filaments at high feed forces and pressures, which tend to compress the soft filament and may result in jamming. Using higher feed forces and pressures may allow for a greater range of process conditions and may provide a consistent jacket around the substrate. In particular, use of the first guide sheath 224 extending at least partially into the first filament port 216 may facilitate the use of softer filament and greater "push-ability." Additionally, or alternatively, the use of the support element 228 may also facilitate the use of softer filament and greater "push-ability." In other embodiments, the apparatus 200 may include a screw or static mixer to help push a softer filament. In other words, the screw or static mixer may provide a cavity for softer filament material to be moved forward between the threads of the screw.

Figure 3:
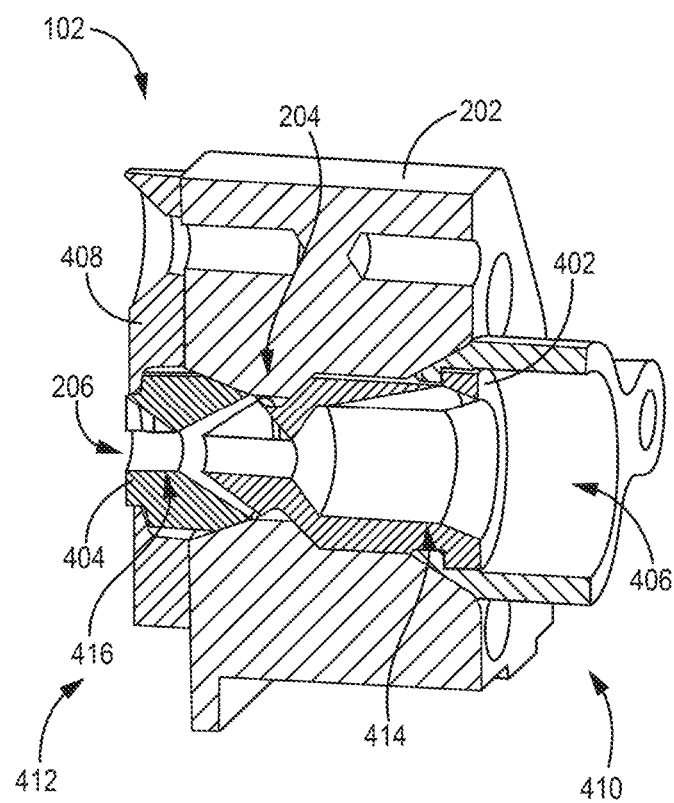
FIG. 3 is a conceptual diagram of an illustrative heating cartridge for use with, for example, the additive manufacturing system of FIG. 1.

FIG. 3 shows a partial cross-sectional side view of one example of the heating cartridge 102. The heating cartridge 102 or the heating block 202 may extend from a proximal side 410 to a distal side 412. In some embodiments, the heating cartridge 102 may include one or more of the heating block 202, an inlet die 402 coupled to the proximal side 410 of the heating block, an outlet die 404 coupled to the distal side 412 of the heating block, a proximal retaining plate 406 to facilitate retaining the inlet die adjacent to the heating block, and a distal retaining plate 408 to facilitate retaining the outlet die adjacent to the heating block.

The inlet die 402 and the outlet die 404 may be retained in any suitable manner. In the illustrated embodiment, the outlet die 404 may be retained by a distal shoulder of the distal retaining plate 408. In some embodiments, the inlet die 402 may be retained by the proximal retaining plate 406 between a distal shoulder of the proximal retaining plate 406 and a fastener, such as a nut with a lumen extending through, which may be threaded to the retaining plate to engage a proximal surface of the inlet die. The retaining plates 406, 408 may be fastened to the heating block 202 in any suitable manner.

The inlet die 402 may at least partially define a substrate inlet port 414. The outlet die 404 may at least partially define a substrate outlet port 416. The inlet die 402 may at least partially define the interior volume 204. The outlet die 404 may at least partially define the interior volume 204. In some embodiments, an exterior surface of the inlet die 402, an interior surface of the outlet die 404, and an interior surface of the heating block 202 may cooperatively define the interior volume 204.

The substrate channel 206 may be described as extending from the proximal side 410 to the distal side 412 of the heating cartridge 102, or vice versa. The substrate channel 206 may extend through the interior volume 204. As shown, the substrate channel 206 may extend through one or more of the proximal retaining plate 406, the inlet die 402, the heating block 202, the outlet die 404, and the distal retaining plate 408.

Figure 4:
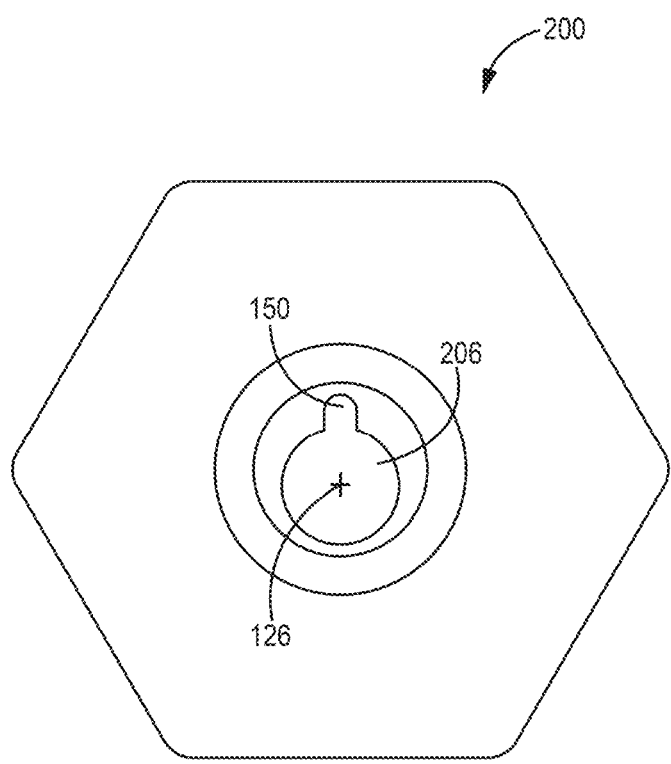
FIG. 4 is a conceptual diagram of an illustrative outlet die that may be used, for example, in the heating cartridge in the additive manufacturing system of FIG. 1.

FIG. 4 depicts an end view of one example of an inlet or outlet die 200 that may be used in the heating cartridge 102 (FIG. 1). The die 200 may define a substrate inlet or outlet port that functions as the substrate channel 206 as described above. The substrate channel 206 may include a pull wire channel 150 that serves to guide a pull wire located within a catheter body formed using the systems described herein. The pull wire may be provided by the wire handling system 107 (see FIG. 1).

Figure 5:
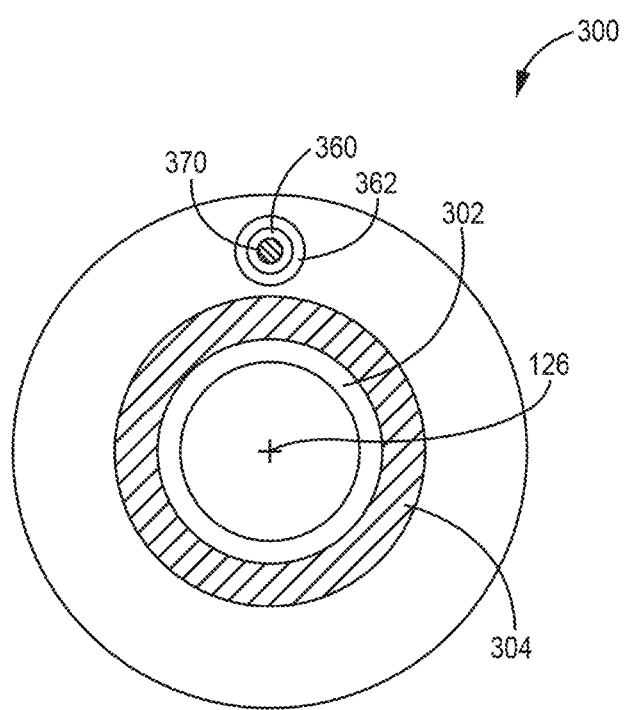
FIG. 5 is a cross-sectional view of one illustrative embodiment of a catheter including a pull wire as described herein, with the cross-sectional view being taken in a plane transverse to the catheter axis extending along the length of the catheter body.

FIG. 5 is a cross-sectional view of one illustrative embodiment of a catheter 300 produced using the systems depicted above with respect to FIGS. 1-4. The catheter 300 includes a catheter body 302 that extends along catheter axis 126 which coincides with the processing axis 126 depicted in connection with the systems of FIGS. 1-4. In one or more embodiments, the catheter axis 126 can be described as being located along the geometric center of the catheter body 302 (which, in the case of a circular cylindrical catheter is in the center of the circle formed in each cross-section of the catheter body taken transverse to the catheter axis). Catheter body 302 may contain other components such as a braided portion 304 as known in the art. Catheter 300 further includes a pull wire 370 located in a pull where lumen 360 extending along the length of the catheter body 302. Pull wire lumen 360 may be formed by a pull wire body 362 may also be incorporated into the catheter body 302. The pull wire 370 is configured to move within the pull wire lumen 360 such that the catheter body 302 of catheter 300 deflects to form one or more curves when the pull wire 370 is placed in tension as described herein.

The pull wire 370 may be made of any suitable material or combination of materials including metals, polymers, composites, etc. provided that the materials are sufficient to transmit the forces necessary to deflect the catheter 300 as described herein.

The catheters described herein may include only a single pull wire such as, e.g., pull wire 370 with the single pull wire being capable of providing multi-plane articulation or deflection of the catheter body 302 in response to tension force is being placed on the pull wire 370.

Multi-plane articulation of one or more embodiments of a catheter due to changes in the location of a pull wire with respect to a catheter axis when moving along the catheter body as described herein can involve changes in the circumferential position of the pull wire relative to the catheter axis as depicted in the illustrative embodiment of FIGS. 6-11. In particular FIG. 6 is a schematic diagram of one illustrative embodiment of a catheter 400 as described herein with the catheter 400 being formed around a substrate 416 as described herein. The pull wire 470 moves around the substrate 416 relative to the catheter axis 126, with the changing location of the pull wire being used to provide multi-plane articulation of the catheter body as described herein. In other words, the location of the pull wire 470 moves around at least a portion of the circumference of the catheter 400 when moving along the elongated catheter 400. Circumferential movement of the pull wires within the catheters described herein may be either or both of clockwise (CW) and counterclockwise (CCW). For example, the pull wire may, in one or more embodiments, move CW over one or more selected portions of the length of the catheters described herein and CCW of one or more other selected portions of the length of the catheters described herein, while in one or more other embodiments of the catheters described herein circumferential movement of the pull wires within a catheter body may be only CW or only CCW. The location of the pull wire 470 is depicted in cross-sectional views in each of FIGS. 7-11. As seen in the cross-sectional figures, the pull wire 470 moves around the substrate 416 relative to the catheter axis 126. In particular, the catheter 400 as seen in cross-sectional views can be characterized in terms of a clock face, with the location of the pull wire 470 moving about the clock face along the length of the catheter 400. In particular, pull wire 470 is located proximate the 6 o'clock position in FIG. 7 and rotates about the catheter axis 126 of catheter 400 to the 12 o'clock position at FIG. 8. At FIG. 9 the pull wire 470 has moved to the 9 o'clock position within the catheter 400, and at FIG. 10, the pull wire 470 has moved to the 6 o'clock position. In FIG. 11, the pull wire 470 has moved to the 3 o'clock position.

Reviewing FIGS. 6-11 shows how the pull wire 470 progresses along and around the catheter 400 which, as described herein, provides for multi-plane deflection or articulation of the catheter when tension is applied to the pull wire 470.

The changes in circumferential position of the pull wire relative to the catheter axis can, in one or more embodiments, be described as occurring over one or more selected portions of the length of the catheter body of the catheter, with the selected portions having a start location and a finish location (when moving from towards a distal end of the catheter). In particular, FIGS. 6-11 depict one illustrative set of changes in circumferential position of pull wire 470 relative to a catheter axis 426 over five different selected portions of the length of the catheter body of catheter 400. The cross-sectional views of FIGS. 7 and 8 depict the changes in circumferential positions of the pull wire 470 at a start location and a finish location over one of the selected portions (noting that the circumferential position of the pull wire 470 is constant proximal from line 7-7 in FIG. 6 and constant proximal to and immediately distal from line 8-8 in FIG. 6), FIGS. 8 and 10 depicting the changes in circumferential position of the pull wire 470 at the start location and the finish location over another one of the selected portions (FIG. 9 depicting the circumferential position of the pull wire 470 at an intermediate location between the start and finish locations depicted in FIGS. 8 and 10 and the circumferential position of the pull wire 470 being substantially constant proximal from and distal to line 10-10 in FIG. 6).

Although the changes in circumferential position of the pull wire 470 are described in terms of clock positions, in one or more embodiments the change in circumferential position of the pull wires from the start location to the finish location within a selected portion of the length of the catheter bodies as described herein can be controlled in increments as small as 1 degree (measured relative to a catheter axis). As a result, the circumferential positions of pull wires over the lengths of selected portions of the catheter bodies can be controlled to move over an arc of, e.g., 1 degree or more, 2 degrees or more, 3 degrees or more, 4 degrees or more, or 5 degrees or more at a low end. Even such relatively small changes in circumferential position yields improvements in forming selected curve deflections in multiple planes as described herein. These selected changes in circumferential position of pull wires can be distinguished from random variations in circumferential position of a pull wire that can occur during manufacturing of conventional catheter bodies. In those instances, the variations in circumferential position are random, i.e., not controlled and, essentially, a function of native (uncontrolled) forces present in the manufacturing process.

At the upper end, the pull wires in catheter bodies as described herein may, in one or more embodiments, move circumferentially over an arc of X+(n*360) degrees or less, where X is 360 degrees or less, 330 degrees or less, 300 degrees or less, 270 degrees or less, 240 degrees or less, 210 degrees or less, 180 degrees or less, 150 degrees or less, 135 degrees or less, 120 degrees or less, 90 degrees or less, 75 degrees or less, 60 degrees or less, 45 degrees or less, 30 degrees or less, 15 degrees or less, 10 degrees or less, or 5 degrees or less over the lengths of the selected portions of the catheter bodies. Larger scale changes in the circumferential position of pull wires in one or more embodiments of catheters as described herein can assist in in forming selected curve deflections in multiple planes as described herein. Adding one or more complete revolutions of the pull wire about a catheter axis in one or more selected portions of catheters as described herein can assist with controlling the order in which the curve deflections form as a pull wires is placed in tension as described herein and/or also assist with the retention of curve deflections and/or reversal of curve deflection after the pull wire placed in tension to form the curve deflections is no longer held in tension within a catheter. Those changes in curve deflection formation order, retention, and/or reversal may be provided due to, e.g., increases in friction between the pull wires and the lumens in which they are located, permanent deformation of the pull wires as a result of curve deflection, etc.

The selected portions of the catheter bodies over which the changes in circumferential position of pull wires as described herein may, in one or more embodiments, have lengths that are limited to, for example, 50% or less, 40% or less, 30% or less, 20% or less, or 10% or less of the total lengths of the catheter bodies as measured from their proximal ends to their distal ends. In other words, the circumferential pull wire position changes can be controlled over both relatively long and relatively short portions of the catheter bodies of catheters as described herein. In terms of specific lengths, in one or more embodiments, the lengths of the selected portions over which the circumferential pull wire position changes occur can, at a lower end, be, e.g., 5 millimeters (mm) or more, 10 mm or more, 15 mm or more, or 20 mm or more. At an upper end, the lengths of the selected portions over which the circumferential pull wire position changes occur can, in one or more embodiments, be, e.g., 200 mm or less, 160 mm or less, 120 mm or less, or 100 mm or less.

Another feature shown in FIG. 6 is the anchor 472 located at the distal end of the pull wire 470. The anchor 472 fixes the position of the distal end of the pull wire 470 relative to the catheter 400 such that tension forces can be applied to the pull wire that result in deflection of portions of the catheter body of catheter 400. The anchor 472 may take any suitable form examples of which may include, for example, a crimped section of a hypo tube located on an otherwise flexible pull wire, rings, barbs, discs, bulbs, etc. essentially any construction that provides for mechanical fixation of the distal end of the pull wire 470 within the catheter 400 is acceptable.

Moreover, as described herein, although the anchor 472 of pull wire 470 is depicted as proximate the distal end 408 of the catheter 400, the anchor may be located any selected location along the catheter 400 that may or may not be proximate the distal end 408 of the catheter. Location of the anchor 472 is however, required, to be distal any section in which multi-plane articulation or deflection of the catheter 400 is desired because the pull wire 470 cannot transmit force past its distal end within the catheter 400.

While movement or change of position of a pull wire within a catheter to provide for deflection of a catheter as described herein can be circumferentially as discussed above in connection with FIGS. 6-11, multi-plane articulation of one or more portions of a catheter as described herein can also be achieved by moving the position of a pull wire radially such that the radial position of the pull wire with respect to a catheter axis moves towards and/or away from the catheter axis.

Another illustrative embodiment of a catheter 400' in which a pull wire 470' moves towards and away from a catheter axis is depicted in FIG. 12A-12D. FIG. 12A is a schematic diagram of the catheter 400', with the catheter 400' being formed around a substrate 416' as described herein. Pull wire 470' extends through the catheter 400' towards an anchor 472' located at the distal end of the pull wire 470', with the anchor 472' being located proximate the distal end 408' of the catheter 400' in the depicted embodiment.

The radial position of the pull wire 470' is depicted in cross-sectional views in each of FIGS. 12B-12D. The pull wire 470' in catheter 400' moves radially towards and away from the catheter axis 426 when moving along the catheter 400' towards the distal end 408' of the catheter 400'. The changing radial position of the pull wire 470' can, in one or more embodiments, be used to provide multi-plane articulation of the catheter 400' when the pull wire 470' is placed in tension within the catheter 400' as described herein.

In particular, the pull wire 470' moves towards the catheter axis 426' when moving between the locations of section lines 12B-12B and 12C-12C. Pull wire 470' also moves away from the catheter axis 426' when moving between the locations of section lines 12C-12C and 12D-12D. As seen in the cross-sectional views of FIGS. 12B-12D, the circumferential (or clock) position of the pull wire 470' does not change in the embodiment of catheter 400'. The changes in radial positions can be described as occurring over selected portions of the length of the catheter 400' as depicted in FIG. 12A, with section line 12B-12B defining the start location of a selected portion extending to a finish location at section line 12C-12C and another selected portion of the length of catheter 400' extending from a start location at section line 12C-12C to a finish location at section line 12D-12D.

The selected portions of the catheter bodies over which the changes in radial position of pull wires as described herein may, in one or more embodiments, have lengths that are limited to, for example, 50% or less, 40% or less, 30% or less, 20% or less, or 10% or less of the total lengths of the catheter bodies as measured from their proximal ends to their distal ends. In other words, the radial pull wire position changes can be controlled over both relatively long and relatively short portions of the catheter bodies of catheters as described herein. In terms of specific lengths, in one or more embodiments, the lengths of the selected portions over which the radial pull wire position changes occur can, at a lower end, be, e.g., 5 millimeters (mm) or more, 10 mm or more, 15 mm or more, or 20 mm or more. At an upper end, the lengths of the selected portions over which the radial pull wire position changes occur can, in one or more embodiments, be, e.g., 200 mm or less, 160 mm or less, 120 mm or less, or 100 mm or less.

Although FIGS. 6-11 depict changes in the circumferential position of a pull wire while the radial position of the pull wire (with respect to the catheter axis) remains constant and FIG. 12A-12D depict changes in the radial position of the a pull wire while the circumferential position of the pull wire remains constant, one or more alternative embodiments of catheters as described herein may include pull wires that change in both circumferential and radial position when needed to facilitate multi-plane deflection of the catheters when the pull wire is placed in tension.

FIGS. 13A-13C depict a selected portion of the length of one such illustrative embodiment of a catheter in which both the circumferential and radial positions of a pull wire change over a selected portion of the length of the catheter body, with FIGS. 13B and 13C being cross-sectional views of the catheter of FIG. 13A taken in planes transverse to the catheter axis to illustrate the changes in both circumferential and radial positions of the pull wire within the catheter body.

The catheter 400" of FIGS. 13A-13C includes a pull wire 470" that extends through the depicted portion of the catheter body of the catheter 400". The pull wire 470" moves circumferentially around the catheter axis 426" when moving from the start location of the selected portion of the length of the catheter body of catheter 400 (where the start location corresponds to the location of line 13B-13B in FIG. 13A) to the finish location of the selected portion (where the finish location corresponds to the location of line 13C-13C in FIG. 13A).

As depicted in FIGS. 13A and 13B, the pull wire 470" is located in what can be described as a 6 o'clock position at the start location and the 10 o'clock position at the finish location. To move to the finish location from the start location, the pull wire 470" may move clockwise (CW) about catheter axis 426" over an arc 120 degrees or, alternatively, counterclockwise (CCW) over an arc of 240 degrees.

In addition to moving circumferentially between the start and finish locations over an arc of 120 degrees CW or 240 degrees CCW, the pull wire 470" also completes two (2) full rotations/revolutions about the catheter axis 426" when moving from the start location to the finish location. As a result, the pull wire 470" can be described as moving circumferentially about the catheter axis 426" (between the start and finish locations) either 120+(2*360) degrees CW or 240+(2*360) CCW. With reference to FIG. 13A, the pull wire 470" completes one full rotation/revolution from the start location at section line 13B-13B to location R1 and a second full rotation/revolution between location R1 and location R2.

As described herein, the additional complete revolutions of the pull wire about the catheter axis 426" in the selected portion of the catheter 400" can assist with controlling the order in which the curve deflections form in the depicted selection portion of the catheter 400" as compared to other selected portions of the catheter 400" (not shown) as the pull wire 470" is placed in tension as described herein and/or also assist with the retention of curve deflection and/or reversal of the curve deflection in the selected portion after the pull wire 470" is no longer held in tension within catheter 400". Changes in curve formation order, retention, and/or reversal may be provided due to, e.g., increases in friction between the pull wire 470" and a lumen in which it is located, permanent deformation of the pull wire 470" as a result of curve deflection, etc.

In addition to the changes in circumferential position of the pull wire 470" depicted in FIGS. 13A-13C, the radial location of the pull wire 470" relative to the catheter axis 426" is also depicted in this illustrative embodiment. In particular, the pull wire 470" is located closer to the catheter axis 426" at the finish location depicted in FIG. 13C than at the start location depicted in FIG. 13B. The changing radial position of the pull wire 470" can assist in providing curve deflection and resulting multi-plane articulation of the catheter 400" when the pull wire 470" is placed in tension within the catheter 400" as described herein.

Another illustrative embodiment of a catheter as described herein is depicted in FIGS. 14-16C. The catheter 500 is depicted in a perspective view in FIG. 14 after a pull wire located within the catheter body is placed in tension, while FIG. 15 is a schematic diagram of the catheter 500 before the catheter 500 is placed in tension using the pull wire. The axes of a three dimensional Cartesian coordinate system are provided in each of FIGS. 14-16C to assist with an understanding of the curves formed by selected portions of the catheter 500 using a pull wire as described herein.

The catheter 500 includes an elongated catheter body 510 that extends along a catheter axis 526 from a proximal end 501 to a distal end 502. A pull wire 570 extends through the catheter 500 as described in connection with other embodiments of catheters as described herein. Although the guide wire 570 may, as described above, follow a path in which its position changes along the length of the catheter 500 to achieve selected curve deflection in multiple planes such that three-dimensional shapes can be formed when the pull wire 570 extending through the catheter 500 is placed in tension sufficient to cause the selected deflection, that feature is not required in all catheters described herein.

Rather, catheter 500 is one illustrative embodiment of catheters as described herein in which selected curve deflection in multiple planes to provide three-dimensional shapes can be achieved using pull wire 570 by changing the rigidity/stiffness of selected portions of the catheter body 510 when the pull wire 570 is placed in tension along the length of the catheter 500. Changes in rigidity of selected portions of the catheter body 510 can, alone, provide selected curve deflection in multiple planes (although those properties can potentially be enhanced by changing the location of the pull wire 570 within the catheter body 510 as described in connection with other embodiments herein).

In the depicted embodiment of catheter 500, a proximal portion of the catheter body may be found between proximal end 501 and location 581 along the length of the catheter body 510. Catheter body 510 also includes a portion between locations 581 and 582, another portion between location 582 and location 583, another portion between location 583 and location 584, and a final or distal portion between location 584 and the distal end 502 of the catheter body 510. In the depicted illustrative embodiment, the pull wire 570 is attached to an anchor located within the final or distal portion of the catheter body 510.

The portion of the catheter body 510 between locations 581 and 582 is configured to form a curved portion when the pull wire 570 is placed in tension between the anchor to which pull wire 570 is attached is placed in tension along the length of the catheter body 510. Similarly, the portion of the catheter body 510 between locations 583 and 584 is also configured to form a curved portion when the pull wire 570 is placed in tension as described herein.

In one or more embodiments, the changes in rigidity can be described solely by changes in the elastic modulus of the materials used to form each selected portion of the catheters as described herein (where, e.g., the moment of inertia (I) remains substantially constant between the selected portions). With respect to the illustrative embodiment of catheter 500 in which the moment of inertia remains substantially constant along the length of the catheter, the elastic modulus in the portion of the catheter 500 extending between the proximal end 501 and location 581, the portion of the catheter 500 between locations 582 and 583, and the portion of the catheter 500 between locations 584 and the distal end 502 may all be formed of material with a relatively high modulus of elasticity so that the resulting portions of the catheter have a relatively high rigidity and are, therefore, relatively resistant to forming curves when the pull wire is placed in tension. The anchor at the end of the pull wire 570 is located distal of location 584 such that the anchor is contained with the relatively high elastic modulus material in that portion of the catheter body 510.

Conversely, the portion of the catheter 500 between location 583 and 584 as well as the portion of the catheter between locations 581 and 582 are constructed of materials that have a relatively low elastic modulus such that those portions of the catheter 500 have a relatively low rigidity and are, therefore more susceptible to forming curves when a pull wire is placed in tension as described herein. Approximately the last half of the portion extending distal from location 584 is preferably constructed of the relatively low elastic modulus material described above to provide a softer tip at the distal end 502 that is less likely to damage tissue.

By way of example only, i.e., not to be construed as limiting in any sense, the portions 501-581, 582-583, and the portion just distal from location 584 may all be constructed of material(s) having a durometer of 72D with an elastic modulus of 513 MPa, while portion 583-584 (along with the tip at the distal end 502) is constructed of material(s) having a durometer of 35D and an elastic modulus of 21 MPa. When manufactured using an additive manufacturing process as described herein, there will be transitions between the different selected portions in which the catheter body is a blend of the different materials, but those transitions are typically kept as short as possible.

One additional feature of the catheter 500 depicted in FIGS. 14-16C is that the portion of catheter 500 between locations 581 and 582 is that the catheter body includes composite structure in which spline of relatively high elastic modulus material is provided, with the remainder of the catheter body 510 constructed of relatively low elastic modulus material. This construction may, in one or more embodiments, provide for a curve that has a relatively large radius of curvature as depicted in, e.g., FIGS. 14 and 16A, when the pull wire extending through the catheter 500 is placed in tension as described herein.

The cross-section view seen in FIG. 15A (taken along line 15A-15A in FIG. 15) shows the spline 588 and remainder 586 of the catheter body 510 with, as noted above, the spline 588 being constructed of the relatively high elastic modulus material used in portion 501-581 and the remainder 586 of the catheter body 510 being constructed of the relatively low elastic modulus material used in portion 583-584.

The cross-sectional view of FIG. 15A also depicts the location of the pull wire 570 relative to both the catheter axis 526 and the spline 588. The arrangement of spline 588 and remainder 586, coupled with the location of the pull wire 570 relative to those features and the catheter axis 526 provides a curve that has a relatively large radius of curvature as depicted in, e.g., FIGS. 14 and 16A, when the pull wire extending through the catheter 500 is placed in tension as described herein.

Yet another feature found in the illustrative embodiment of catheter 500 is that the pull wire 570 moves circumferentially (relative to the catheter axis 526) in the portion 582-583 and also in the portion 583-584. By way of example only, i.e., not to be construed as limiting in any sense, the pull wire 570 moves over an arc of 40 degrees around the catheter axis 526 from location 582 to 583. By way of example only, i.e., not to be construed as limiting in any sense, the pull wire 570 moves over an arc of 25 degrees around the catheter axis 526 from location 583 to 584. These changes in circumferential position assist in forming the out of plane curves when moving from the curve between locations 581 and 582 to the more distal portions of the catheter 500.

By way of example only, i.e., not to be construed as limiting in any sense, the catheter 500 may be constructed with portions having the following lengths: 400 mm from the proximal end 501 to location 581, 120 mm from location 581 to location 582, 25 mm from location 582 to location 583, 55 mm from location 583 to location 584, 20 mm from location 584 to the distal end 502. Catheters as described herein may, of course, have portions of any suitable length depending on their intended use.

The various curved portions of the catheter body 510 result in a catheter 500 that, as described herein, deflects in multiple planes to provide a three-dimensional shape. The three-dimensional nature of the shapes formed by catheters as described herein can, and one or more embodiments, be described with respect to projections on the different planes forming a three dimensional Cartesian coordinate system.

Figure 16A:
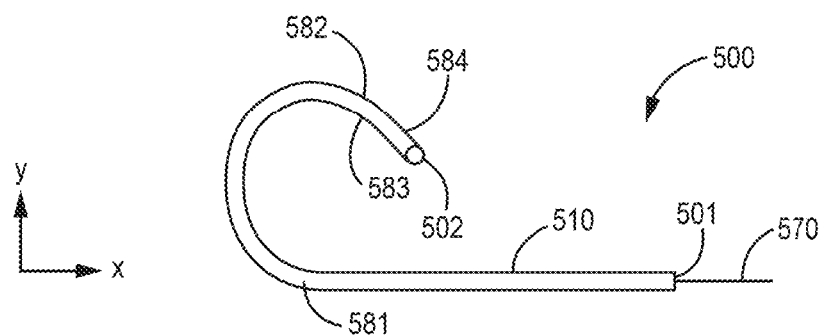
FIG. 16A depicts the catheter of FIG. 14 as projected onto the XY plane of a three dimensional Cartesian coordinate system.
Figure 16B:
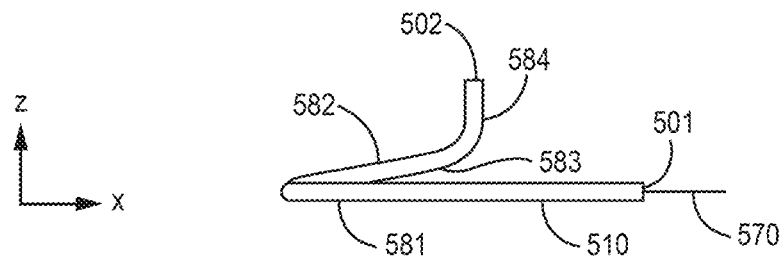
FIG. 16B depicts the catheter of FIG. 14 as projected onto the XZ plane of a three dimensional Cartesian coordinate system.
Figure 16C:
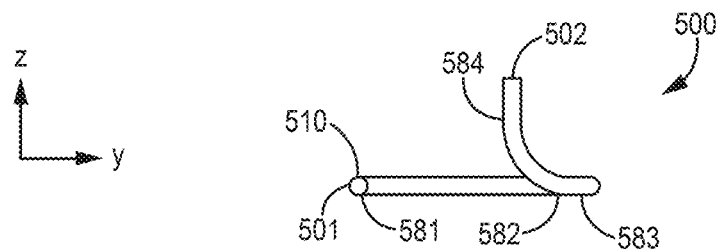
FIG. 16C depicts the catheter of FIG. 14 as projected onto the YZ plane of a three dimensional Cartesian coordinate system.

In the depicted illustrative embodiment of catheter 500, the curved portion of catheter body 510 between locations 581 and 582 forms a curve when the curved portion between locations 581 and 582 is projected onto the X-Y plane along a Z axis of the three-dimensional Cartesian coordinate system as depicted in FIG. 16A. The catheter body 510 also forms a curved portion between locations 583 and 584 when the curved portion between locations 583 and 584 is projected onto the X-Z plane along the Y-axis as depicted in FIG. 16B. Further, the curved portion of the catheter body 510 between locations 583 and 584 also forms a curve when projected onto the Y-Z plane along the X axis as depicted in FIG. 16C.

One or more embodiments, the radius of curvature of the different curved portions of the catheters described herein may be the same or different. In the depicted illustrative embodiment, the curve between locations 581 and 582 on catheter body 510 has a radius of curvature when projected onto the X-Y plane as seen in FIG. 14 that is different than the radius of curvature of the curve formed by a projection of the portion of catheter body 510 between locations 583 and 584 onto the X-Z plane as seen in FIG. 15.

The various properties of rigidity in each of the portions of the catheters described herein may be chosen to provide for a selected order of formation. In other words, the order in which the catheter body portions between the various locations form curves may be selected by tailoring the rigidity in each of the portions to achieve that function. For example, the rigidity of the portion of the catheter between locations 583 and 584 as compared to the rigidity of the portion of the catheter body 510 between locations 581 and 582 may be selected such that the portion of the catheter body 510 between locations 583 and 584 forms the depicted curve before or after the portion of the catheter body 510 between locations 581 and 582 forms the curve depicted in FIGS. 14 and 16A-16C.

Figure 17:
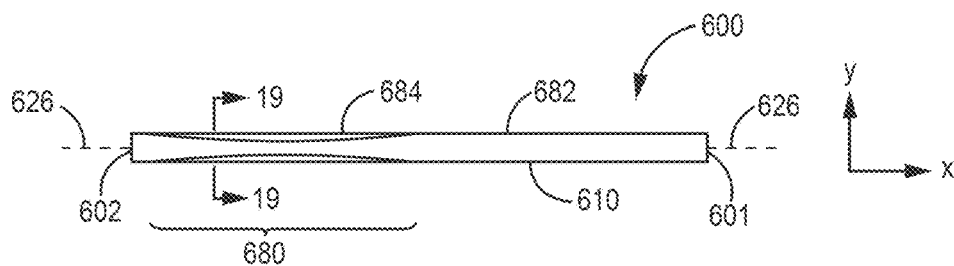
FIG. 17 depicts another illustrative embodiment of a catheter as described herein in a relaxed state.
Figure 18:
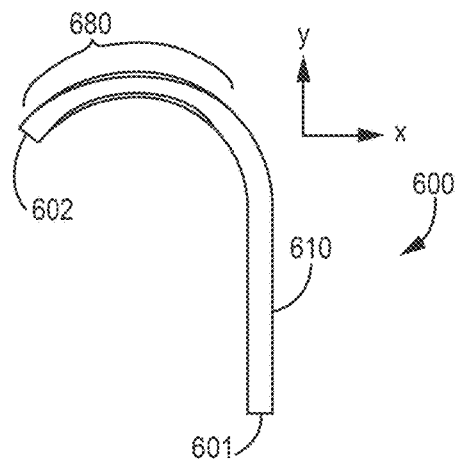
FIG. 18 depicts the catheter of FIG. 17 after a pull wire extending through the catheter body is pulled to place the catheter body in tension as described herein.
Figure 19:
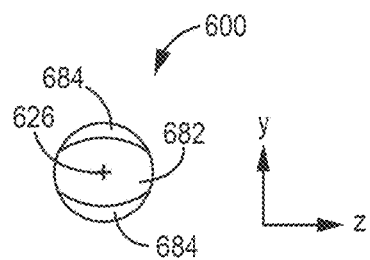
FIG. 19 it is a cross-sectional view of the catheter of FIG. 17 taken along line 19-19 in FIG. 17.

Another illustrative embodiment of a catheter 600 as described herein is depicted in FIGS. 17-19. The catheter 600 includes a catheter body 610 that extends from a proximal end 601 to a distal end 602 along a catheter axis 626. In particular, FIG. 17 depicts the catheter body 610 at rest, i.e., when a pull wire located within catheter body 610 is not in tension. FIG. 18 depicts the catheter body 610 of catheter 600 after the catheter body 610 is placed in tension using, e.g., a pull wire as described herein, and FIG. 19 is a cross-sectional view of the catheter body 610 taken along line 19-19 in FIG. 17.

Although not shown, a pull wire extends through the catheter body as discussed in connection with other embodiments of catheters as described herein. Other features such as lumens, etc., common to catheters used as medical devices may also be included in the catheter body 610 of catheter 600 but are not described herein.

The catheter body 610 of catheter 600 is manufactured of multiple materials that are combined in a manner that controls the rigidity of portions of the catheter body 610 as described herein. In the depicted embodiment catheter body 610 includes a portion 680 configured to form a curve when the catheter body is placed in tension using, e.g., a pull wire as described herein. The depicted embodiment of portion 680 of catheter body 610 includes a core 682 and a jacket 684 that, in the depicted embodiment, is provided in two portions located on opposite sides of the core 682 of catheter body 610.

Although described as a jacket, jacket 682 may be provided in multiple portions as depicted in FIGS. 17-19 and need not necessarily surround the core 682 of the catheter body 610. The portions of the jacket material may be uniformly or non-uniformly distributed about the catheter axis 626 to provide a selected curvature to the catheter body 610 when the catheter body 610 is placed in tension using, e.g., a pull wire as described herein. In particular, the depicted distribution of jacket material forming jacket 684 about core 682 may result in formation of a curve in portion 680 that lies primarily in an XY plane of a three dimensional Cartesian coordinate system as seen in FIG. 18.

The core 682 and the jacket 684 may be manufactured of different materials, with the core 682 being manufactured of a core material while the jacket 684 is manufactured a jacket material. Although described as singular materials, i.e., a core material or a jacket material, one or both of the core material and jacket material may, in fact, be a composite of two or more different materials or components provided together to form the core 682 and/or the jacket portions 684.

In one or more embodiments, the modulus of elasticity of the core material forming core 682 and the jacket material forming jacket 684 are different. For example, in one or more embodiments, the modulus of elasticity of the jacket material may be less than the modulus of elasticity of the core material. Due to the lower modulus of elasticity of the jacket material in portion 680 of catheter body 610, placing the catheter body 610 in tension using, for example, a pull wire as described herein, causes the catheter body 610 to form a curve as seen in, e.g., FIG. 18.

Figure 20:
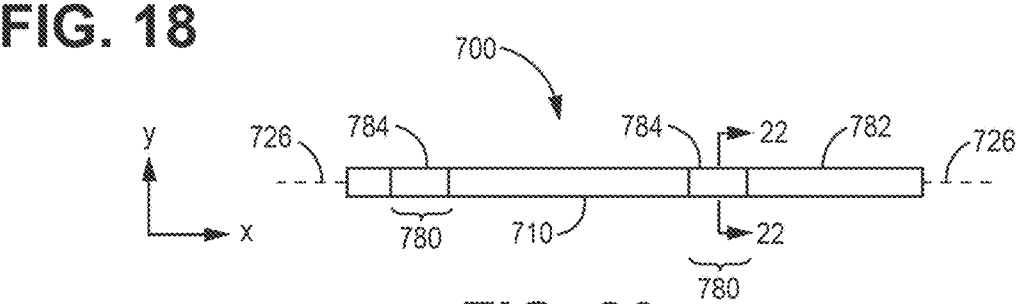
FIG. 20 depicts another illustrative embodiment of a catheter as described herein in a relaxed state.
Figure 21:
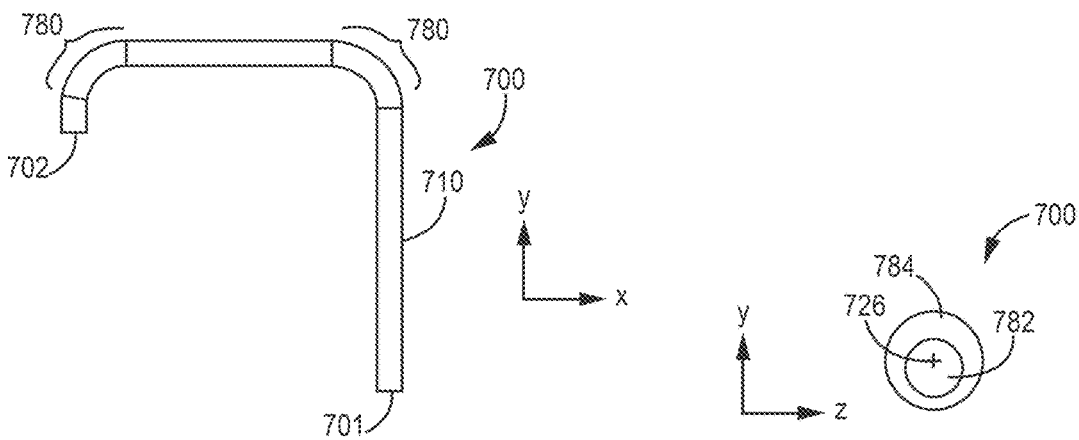
FIG. 21 depicts the catheter of FIG. 20 after a pull wire extending through the catheter body is pulled to place the catheter body in tension as described herein.
Figure 22:
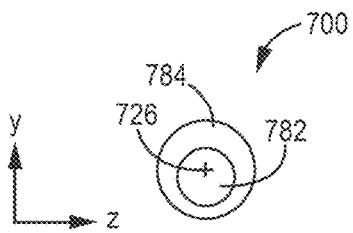
FIG. 22 is a cross-sectional view of the catheter of FIG. 20 taken along line 22-22 in FIG. 20.

Another illustrative embodiment of a catheter 700 including a catheter body 710 extending from a proximal end 701 to a distal end 702 is depicted in FIGS. 20-22. The catheter 700 includes a catheter body 710 that extends from a proximal end 701 to a distal end 702 along a catheter axis 726. In particular, FIG. 20 depicts the catheter body 710 at rest, i.e., when a pull wire located within catheter body 710 is not in tension. FIG. 21 depicts the catheter body 710 of catheter 700 after the catheter body 710 is placed in tension using, e.g., a pull wire as described herein. FIG. 22 is a cross-sectional view of the catheter body 710 taken along line 22-22 in FIG. 20.

Although not shown in connection with catheter 700, a pull wire extends through the catheter body 710 as discussed in connection with other embodiments of catheters as described herein. Other features such as lumens, etc., common to catheters used as medical devices may also be included in the catheter body 710 of catheter 700 but are not described herein.

The catheter body 710 of catheter 700 is also manufactured of multiple materials that are combined in a manner that controls the rigidity of portions of the catheter body 710 as described herein. The catheter body 710 of catheter 700 includes two portions 780, each of which forms a curve when the catheter body 710 is placed in tension using, e.g., a pull wire as described herein (see, e.g., FIG. 21). Both of the portions 780 and catheter body 710 include a core 782 and a jacket 784 that, in the depicted embodiment, surrounds the core 782 as seen in, e.g., the cross-sectional view of FIG. 22.

Although the portions of catheter body 710 including a jacket 784 may surround the core 782, the material forming the jacket 784 may be non-uniformly distributed about the catheter axis 726 to provide a selected curvature in the portion 780 of the catheter body 710 when the catheter body 710 is placed in tension using, e.g., a pull wire as described herein. In the depicted illustrative embodiment, the core 782 is offset from the catheter axis 726 such that the jacket 784 is thicker in some directions than other directions. In FIG. 22, core 782 is shifted downward such that more of the material forming jacket 784 is located above the core 782 and less material of the jacket 784 is located below the core 726. Such non-uniform distribution of the material forming jacket 784 about the core 782 may result in the formation of a selected curve in portion 780 of catheter body 710. In the depicted embodiment, the distribution of material forming jacket 784 about core 782 may provide a curve that lies primarily in an XY plane of a three dimensional Cartesian coordinate system as seen in FIG. 21.

As discussed above in connection with other catheters described herein, the core 782 and jacket 784 may be manufactured of different materials, with the core 782 being manufactured of a core material, while jacket 784 is manufactured of a jacket material. Although described as singular materials, i.e., a core material or a jacket material, one or both of the core material and the jacket material may, in fact, be a composite of two or more different materials or components provided together to form the core 782 and/or the jackets 784.

In one or more embodiments, the modulus of elasticity of the core material forming core 782 and the jacket material forming jacket 784 are different. For example, in one or more embodiments, the modulus of elasticity of the jacket material may be less than the modulus of elasticity of the core material. Due to the lower modulus of elasticity of the jacket material in portions 780 of catheter body 710, placing the catheter body 710 in tension using, for example, a pull wire as described herein, causes the catheter body 710 to form curves as seen in FIG. 21.

Another illustrative embodiment of a catheter 800 including a catheter body 810 extending from a proximal end 801 to a distal end 802 along a catheter axis 826 is depicted in FIGS. 23-25. In particular, FIG. 23 depicts the catheter body 810 at rest, i.e., when a pull wire located within catheter body 810 is not in tension. FIG. 24 depicts the catheter body 810 of catheter 800 after the catheter body 810 is placed in tension using, e.g., a pull wire as described herein. FIG. 25 is a cross-sectional view of the catheter body 810 taken along line 25-25 in FIG. 23.

Although not shown in connection with catheter 800, a pull wire extends through the catheter body 810 as discussed in connection with other embodiments of catheters described herein. Other features such as lumens, etc., common to catheters used as medical devices may also be included in or on the catheter body 810 of catheter 800 but are not described herein.

The catheter body 810 of catheter 800 includes a portion 880 in which the rigidity of the catheter body 810 is reduced as compared to portions of the catheter adjacent to portion 880. The reduced rigidity in portion 880 is configured to form a curve when the catheter body 810 is placed in tension using, e.g., a pull wire as described herein. The rigidity of portion 880 of catheter body 810 is, in the depicted illustrative embodiment, reduced by reducing the amount of material in the portion 880 of catheter body 810. Reducing the amount of material can be used to reduce the moment of inertia (I) of the portion 880 of the catheter body 810 to, consequently, reduce the rigidity of portion 880 to promote the formation of a curve.

Because the depicted catheter body 810 is generally circular in its cross-sectional shape, the amount of material is reduced by reducing the diameter of the catheter body 810 in portion 880. With reference to FIG. 25, the reduced diameter in portion 880 catheter body 810 is seen in the different diameters provided by exterior surface 883 in portion 880 as compared to exterior surface 803 in the portion of catheter body 810 proximal to the portion 880.

In catheter bodies having noncircular cross-sectional shapes, the cross-sectional area of the catheter body in a portion or portions 880 in which a curve is to be formed may be reduced in a manner calculated to result in the formation of a curve in the portion or portions 880 when the catheter body 810 is placed in tension as described herein. The cross-sectional area in such embodiments may be defined as a cross-sectional area in a cross-section taken in a plane transverse to the catheter axis, e.g., catheter axis 826 in connection with catheter 800.

In the depicted illustrative embodiment of catheter 800, the reduced rigidity in portion 880 forms a selected curve in portion 880 of catheter body 810. In the depicted embodiment, the portion 880 provides a curve that lies primarily in an XY plane of a three dimensional Cartesian coordinate system seen in FIGS. 23-25.

Although the catheter body 810 of catheter 800 is depicted as being made of a single material, it should be understood that alternative embodiments of catheters in which the cross-sectional area in one or more selected portions is reduced to form a selected curve when the catheter body is placed in tension as described herein may include catheter bodies including portions that are manufactured of two or more different materials or components in addition to having a change in cross-sectional area with both the material/component selection and the cross-sectional area combining to provide a selected rigidity in the portion or portions of the catheter body such that a selected curve or curves can be formed in those portions when the catheter body is placed in tension as described herein.

While the depicted embodiment of catheter 800 includes a portion 880 in which the amount of material located within portion 880 as compared to the amount of material located in the portion of catheter body outside of portion 880 is gradually changed when moving along catheter axis 826 to achieve a desired curved shape when the catheter body 810 is placed in tension as described herein, illustrative embodiment of catheter 900 includes a catheter body 910 in which material forming the catheter body 910 is reduced in discrete selected areas within portions 980 and 980' to reduce rigidity of the catheter body 910 in portions 980 and 980'.

The catheter 900 depicted in FIGS. 26-29 includes a catheter body 910 extending from a proximal end 901 to a distal end 902 along a catheter axis 926. FIG. 26 depicts the catheter body 910 at rest, i.e., when a pull wire located within the catheter body 910 is not in tension. FIG. 27 depicts the catheter body 910 of catheter 900 after the catheter body 910 is placed in tension using, e.g., a pull wire as described herein. FIG. 28 is a cross-sectional view of the catheter body 910 taken along line 28-28 in FIG. 26. FIG. 29 is a cross-sectional view of the catheter body 910 taken along line 29-29 in FIG. 26.

Although not shown in connection with the catheter 900, a pull wire extends through the catheter body 910 as discussed in connection with other embodiments of catheters described herein. Other features such as lumens, etc., common to catheters used as medical devices may also be included in or on the catheter body 910 of catheter 900 but are not described herein.

The catheter body 910 of catheter 900 includes two different portions 980 and 980' in which the rigidity of the catheter body 910 is reduced as compared to portions of the catheter body 910 adjacent to portions 980 and 980'. The reduced rigidity in portions 980 and 980' are configured to form curves when the catheter body 910 is placed in tension using, e.g., a pull wire as described herein. The rigidity of each of portions 980 and 980' is in the depicted illustrative embodiment, reduced by reducing the amount of material in each of the portions 980 and 980' of catheter body 910. As discussed herein, reducing the amount of material can be used to reduce the moment of inertia (I) of the portions 980 and 980' of the catheter body 910 to, consequently, reduce the rigidity of portions 980 and 980' to promote the formation of curves.

With reference to FIGS. 26 and 28, the portion 980 of catheter body 910 includes cuts or channels that extend partially around the perimeter of the body 910, with cuts 981 being located on an opposite side of the body 910 from cuts 982. Moreover, cuts 981 and 982 on opposite sides of the catheter body 910 are also offset along the catheter axis 926 such that cuts 981 are located proximally relative to the location of cuts 982 along catheter axis 926. The illustrative cuts or channels 981 and 982 represent only one example of removing or reducing the amount of material within the portion 980 of catheter body 910 to reduce the rigidity of the portion 980 to provide a selected curve or shape in portion 980 when the catheter body 910 is placed in tension as described herein. Cuts or channels having many other shapes/profiles/etc. could be used in place of the depicted cuts or channels 981 and 982.

With reference to FIGS. 26 and 29, the portion 980' of catheter body 910 includes cuts or channels 981' on one side of the catheter body 910. The illustrative cuts or channels 981' are another illustrative example of reducing the rigidity of the catheter body 910 in one or more portions to provide a selected curve or shape in portion 980' of catheter body 910 when the catheter body 910 is placed in tension as described herein. Cuts or channels having many other shapes/profiles/etc. could be used in place of the depicted cuts or channels 981' in portion 980' of catheter body 910.

In the depicted illustrative embodiment of catheter 900, the reduced rigidity in portions 980 and 980' of catheter body 910 form selected curves in those portions. In the depicted embodiment, both portions 980 and 980' provide a curve that lies primarily in an XY plane of a three dimensional Cartesian coordinate system seen in FIGS. 26-29.

Although the catheter body 910 of catheter 900 is depicted as being made of a single material, it should be understood that alternative embodiments of catheters in which the cross-sectional area in one or more selected portions is reduced to form a selected curve when the catheter body is placed in tension as described herein may include catheter bodies including portions that are manufactured of two or more different materials or components in addition to having a change in cross-sectional area, with both the material/component selection and the cross-sectional area combining to provide a selected rigidity in the portion or portions of the catheter body such that a select curve or curves can be formed in those portions when the catheter body is placed in tension as described herein.

One illustrative embodiment of a portion 1080 of a catheter body that may be configured to form a curve when placed in tension is depicted in FIGS. 30-31. The catheter portion 1080 as depicted in FIG. 30 is a cross-sectional view depicting a core 1082, a jacket 1084, and a pull wire 1070, the cross-sectional view taken along a plane containing the catheter axis 1026 and the pull wire 1070. FIG. 31 is a cross-sectional view of the catheter portion 1080 taken along line 31-31 in FIG. 30.

Another illustrative embodiment of a portion 1180 of a catheter body configured to form a curve when placed in tension is depicted in FIGS. 32-33. The catheter portion 1180 as depicted in FIG. 32 is a cross-sectional view depicting a core 1182, a jacket 1184, and a pull wire 1170, the cross-sectional view taken along a plane containing the catheter axis 1126 and the pull wire 1170. FIG. 33 is a cross-sectional view of the catheter portion 1180 taken along line 33-33 in FIG. 32.

Differences in the catheter portions 1080 and 1180 are primarily in the distribution of the jackets 1084 and 1184 relative to their respective cores 1082 and 1182. In particular, core 1182 is offset as seen in FIGS. 32-33 relative to the catheter axis 1126 which results in more of the jacket material forming jacket 1184 being located at the bottom of the portion 1180 as seen in the cross-sectional view of FIG. 33. Such nonuniform distribution of the jacket material as compared to the uniform distribution of jacket material forming jacket 1084 of catheter portion 1080 may enhance or inhibit the formation of a curve in catheter portion 1180 as compared to catheter portion 1080 depending on, e.g., the modulus of elasticity of the jacket material forming jacket 1184 as compared to the core material forming core 1182.

FIGS. 34-38 depict one illustrative embodiment of a catheter 1200 manufactured with a pull wire as described herein. The catheter 1200 includes a catheter body 1210 that extends from a proximal end 1201 to a distal end 1202. Although not depicted, the catheter 1200 includes a pull wire that extends through the catheter body 1210 to an anchor located proximate the distal end 1202. The catheter 1200 depicted in FIGS. 34-38 includes two portions which may be referred to as knuckles 1282 and 1284 that are configured to form curved portions when the pull wire extending through the catheter body 1210 is placed in tension as described herein. In one or more embodiments, the portions/knuckles 1282/1284 may have a rigidity relative to adjacent portions of the catheter body 1210 that makes portions/knuckles 1282/1284 configured to provide relatively high levels of deflection or articulation of the catheter body 1210.

The materials used to manufacture the catheter body may be selected for their durometer and/or other physical properties that result in the ability of the portions 1282 and 1284 of catheter body 1210 of catheter 1200 to sharply deflect in response to tension placed on a pull wire extending through the catheter 1200 as described herein. In particular, rapid and or drastic changes in durometer of the materials used to form the catheter body and/or location of those materials around the catheter axis extending through the catheter 1200 at the portions/knuckles 1282 and 1284 can be used to provide for higher rates of deflection as seen in each of the portions/knuckles 1282 and 1284.

As discussed above in connection with the illustrative embodiment of catheter 500 depicted in FIGS. 14-16C, changes in rigidity can be described solely by changes in the elastic modulus of the materials used to form each selected portion of the catheters as described herein (where, e.g., the moment of inertia (I) remains substantially constant between the selected portions).

With respect to the illustrative embodiment of catheter 1200 in which the moment of inertia remains substantially constant along the length of the catheter, the elastic modulus in the portion of the catheter body 1210 extending between the proximal end 1201 and the portion/knuckle 1282, the portion of the catheter body 1210 between portions/knuckles 1282 and 1284, and the portion of the catheter body 1210 distal from portion knuckle 1284 may all be formed of material with a relatively high modulus of elasticity so that the resulting portions of the catheter body 1210 have a relatively high rigidity and are, therefore, relatively resistant to forming curves when a pull wire located in catheter body 1210 is placed in tension. The anchor at the end of the pull wire is located distal of the knuckle 1284 such that the anchor is contained with the relatively high elastic modulus material in that portion of the catheter body 1210.

Conversely, the portions/knuckles 1282 and 1284 of the catheter body 1210 are constructed of materials that have a relatively low elastic modulus such that the portions/knuckles 1282 and 1284 have a relatively low rigidity and are, therefore more susceptible to forming curves when a pull wire is placed in tension as described herein. The most distal portion of the catheter proximal from the distal end 1202 is preferably constructed of the relatively low elastic modulus material described above to provide a softer tip at the distal end 1202 that is less likely to damage tissue.

By way of example only, i.e., not to be construed as limiting in any sense, the portions of the catheter body 1210 outside of the portions/knuckles (and the distal tip 1202) may all be constructed of material(s) having a durometer of 72D with an elastic modulus of 513 MPa, while portions/knuckles 1282 and 1284 (along with the tip at the distal end 1202) are constructed of material(s) having a durometer of 35D and an elastic modulus of 21 MPa. When manufactured using an additive manufacturing process as described herein, there will be transitions between the different selected portions in which the catheter body is a blend of the different materials, but those transitions are typically kept as short as possible.

Although not depicted in these figures, another feature found in the illustrative embodiment of catheter 1200 is that the pull wire moves circumferentially (relative to the catheter axis) in the portion of the catheter body between portions/knuckles 1282 and 1284. By way of example only, i.e., not to be construed as limiting in any sense, the pull wire moves over an arc of 90 degrees around the catheter axis between portions/knuckles 1282 and 1284. That change in circumferential position assists in forming the out of plane curve in portion/knuckle 1284.

By way of example only, i.e., not to be construed as limiting in any sense, the catheter 1200 may be constructed with portions having the following lengths: 400 mm from the proximal end 501 to portion/knuckle 1282, 40 mm within portion/knuckle 1282, 30 mm between portions/knuckles 1282 and 1284, 30 mm within portion/knuckle 1284, and 20 mm from portion/knuckle 1284 to the distal end 1202. Catheters as described herein may, of course, have portions of any suitable length depending on their intended use.

As seen in the progression from FIGS. 34 to 35, tension placed on a pull wire extending through the catheter 1200 results in deflection of both portions/knuckles 1282 and 1284. In FIG. 36, further tension placed on the pull wire results in further deflection of the portions/knuckles 1282 and 1284 with the distal portion/knuckle 1284 rotating the catheter 1200 out of the plane on which the catheter 1200 rests. Further tension placed on the catheter body 1210 using a pull wire in catheter 1200 results in still further deflection of the catheter 1200 at each of the portions/knuckles 1282 and 1284 as depicted in FIG. 37.

The end result as seen in FIG. 38 is a catheter 1200 which deflects in multiple planes when the catheter body 1210 is placed in tension using a pull wire as described herein. The catheter 1200 provides a relatively complex geometric shape using a pull wire as described herein to place the catheter body 1210 in tension along with the use of selected materials at selected portions/knuckles to form curves in one or more desired directions with selected amounts of deflection at each of the portions/knuckles.

Figure 39:
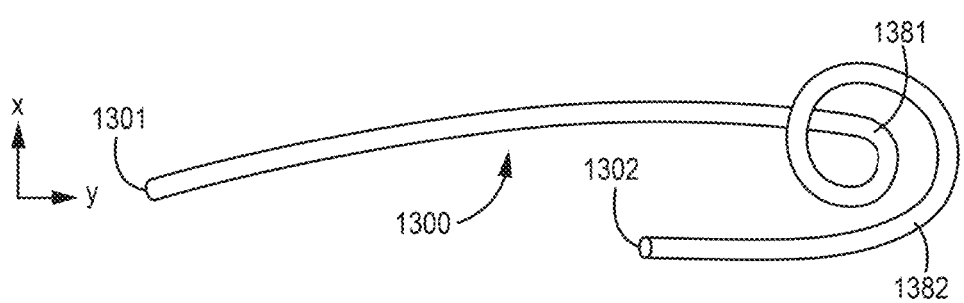
FIG. 39 is a plan view of another illustrative embodiment of a catheter as described herein after deflection of the catheter body using a pull wire as described herein.
Figure 40:
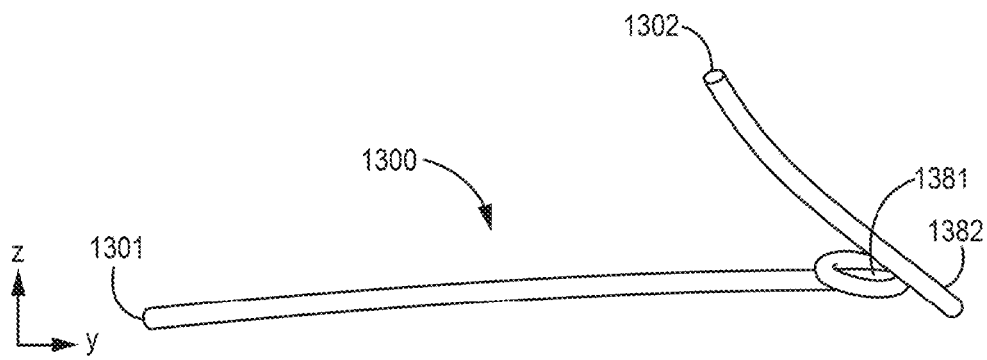
FIG. 40 is a side elevation view of the catheter of FIG. 39.

FIGS. 39-40 depict another illustrative embodiment of a catheter 1300 incorporating a pull wire that, when placed in tension as described herein, can result in deflection of the catheter 1300 in multiple planes. In particular, the catheter 1300 is depicted in a plan view in FIG. 39 corresponding to an X-Y plane while the catheter 1300 is depicted in an elevation view in FIG. 40 corresponding to a Z-Y plane. As seen in FIGS. 39-40 the catheter 1300 deflects in multiple planes and, as described herein, does so using only a single pull wire extending through the catheter body of catheter 1300.

The additive manufacturing systems described herein are capable of depositing higher and lower durometer materials as described herein. Those higher and lower durometer materials applied selectively along with a single pull wire that is selectively placed about the catheter body as described herein provides for multi-plane articulation or deflection of a catheter body incorporating the single pull wire and selected materials. Although similar catheters could be built traditionally by, for example, free-flowing extruded polymer tubing over a liner and braid build, additive manufacturing provides a much greater degree of ability to control the rotation of the pull wire location about the catheter and, further, unique control over the polymer selection and location. Changes in the polymer selection and location can be made using small changes in the G-code of the additive manufacturing system that alter the amount of rotation of the location of the wire, the rate of rotation of the wire and the durometer of the polymer being deposited.

Although not required, in one or more embodiments, curve baking (a traditional technique for polymer catheter shaping), can be used in addition to the additive manufacturing techniques described herein to provide medical devices that form selected curves when, e.g., placed in tension using a pull wire.

Figure 41:
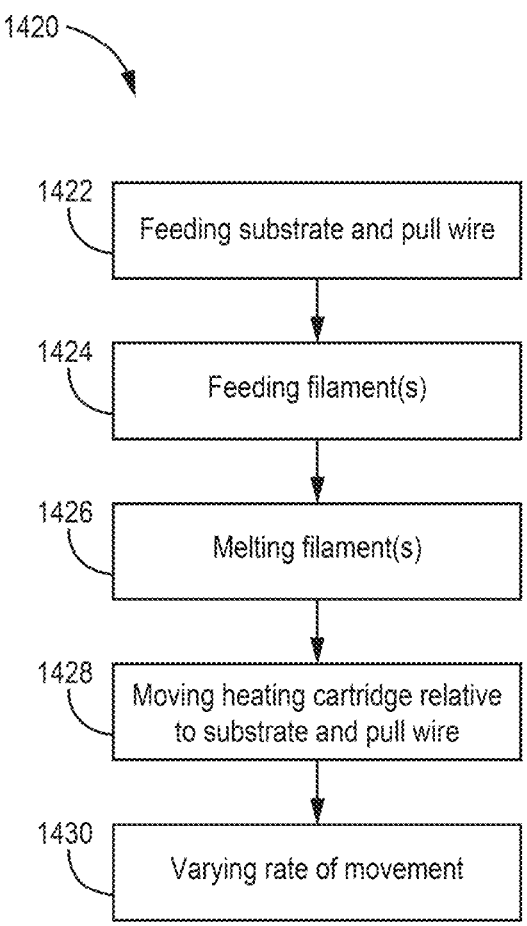
FIG. 41 depicts one illustrative method of manufacturing a catheter as described herein.

FIG. 41 is an example of one illustrative method 1400 of using a system as described herein, e.g., the system 100 (FIG. 1), for additive manufacturing of a catheter as described herein.

The method 1400 may include feeding a substrate and a pull wire 1422 through a substrate channel in a heating cartridge. The substrate channel may be in fluid communication with an interior cavity of the heating cartridge.

The method 1400 may include feeding one or more filaments 1424 to form a layer of material comprising the one or more filaments on the substrate. For example, at least a first filament may be fed through a filament port of the heating cartridge into the interior cavity. In some embodiments, a second filament may be fed through another filament port into the interior cavity. The first and second filaments may be formed of the same or different materials. In some embodiments, the method 1400 may also include adjusting a ratio of the first filament relative to the second filament over a longitudinal distance to change the Shore durometer of the catheter jacket over the longitudinal distance. Doing so may allow for the tailoring of rigidity in selection portions of the medical devices described herein.

The method 1400 may include melting one or more of the filaments 1426, for example, in the interior cavity. Any portion of the filaments contained in the interior cavity may be melted. In some embodiments, a second filament is melted with the first filament.

The method 1400 may include moving the heating cartridge relative to the substrate and the pull wire 1428, for example, at least in a longitudinal direction to form a jacket comprising material from at least the first filament on the substrate. Moving the heating cartridge relative to the substrate and the pull wire may involve moving one or both of the heating cartridge and the substrate/pull wire relative to each other. In most cases, the substrate and pull wire will move in unison (or remain stationary in those embodiments in which the heating cartridge moves). The heating cartridge or substrate/pull wire may also be rotated relative to one another two move the pull wire about the axis of a catheter as described herein.

The jacket formed on the substrate may be formed from material of at least the first filament. In embodiments in which multiple filaments are provided, the jacket may be formed from material of at least a first filament and a second filament. In such embodiments, the materials of the first and second materials may be located in discrete and separate areas on the substrate such that the resulting medical device forms selected curves when placed in tension as described above in connection with the medical devices described herein.

The method 1400 may also include varying the rate of movement 1430 between the heating cartridge and the substrate to define jacket features. For example, the controller may be configured to vary the longitudinal speed of the substrate relative to the heating cartridge. By varying the speed of movement of these components relative to one another during the formation of the jacket, the thickness of the jacket may change over the longitudinal distance. In one or more embodiments, the controller may vary the longitudinal speed of the substrate and pull wire relative to the heating cartridge to define a taper of an outer surface of the jacket. Specifically, in one example, the taper may modify the jacket thickness from 9 French to 7 French. As described herein, changing the size of a medical device body may assist in forming selected curves in the medical device when placed in tension using, e.g., a pull wire.

Further, varying the rate of movement 1430 may also be used to vary the rate at which the location of a pull wire changes within a jacket of a medical device as described herein. With reference to, for example, FIG. 6, changes in rotational speed of the substrate and/or heating cartridge about axis 126 can change the rate at which the pull wire moves around the circumference of the catheter while changes in the translational movement of the substrate and/or heating cartridge along axis 126 can change the rate at which the pull wire moves about the circumference of the catheter. Changes in the rate at which the pull wire moves around the circumference of a catheter as described herein contribute to the deflection or articulation characteristics of the catheter within those areas. In general, slower rates of change in position of the pull wire will result in smoother or less severe deflection of the catheter as compared to faster rates of change in position of the pull wire which will typically result in greater deflection of the catheter. As discussed herein, the rate of change in the circumferential positions of the pull wires can be closely controlled, e.g., in increments as small as 1 degree over a selected portion.

Further, in some embodiments, the method 1400 may also include adjusting a ratio of the first filament relative to the second filament over a longitudinal distance to change the Shore durometer of a jacket over the longitudinal distance. Doing so may change the rigidity of one or more selected portions of the medical device as described herein by changing, for example, changing the modulus of elasticity of the jacket when the materials of the different filaments each have a different modulus of elasticity.

The methods described herein may also include altering the jacket to define jacket features. These jacket features may include any suitable feature as described herein to modify the characteristics of the medical device being formed. For example, the jacket features may allow for interfacing with specific geometries and anatomical features. In other words, the jacket features may allow for controlling friction interfaces as well as create fixation or anchoring components on the external surface of the jacket body (e.g., such that the jacket features may accomplish various "jobs"). Further, the jacket features may assist in holding the medical device steady during device movement, may provide visual markers, or may adjust the mechanical properties of the device.

The jacket features may take the shape of various forms. For example, in one or more embodiments, the jacket features may include threads of differing/variable pitch added to the surface of the jacket. In one or more embodiments, the jacket features may include longitudinal splines added to the external surface of the jacket, e.g., as described in U.S. Pat. App. No. 63/001,832, entitled "3D PRINTED SPLINES ON MEDICAL DEVICES AND METHODS TO MANUFACTURE THE SAME," which is herein incorporated by reference. In one or more embodiments, the jacket features may include elongated structures added to the surface of the jacket to, e.g., change the general shape profile (e.g., wings or two lobed, a triangle, a box/cube, etc.) of the jacket. In one or more embodiments, the jacket features may include intermittent surface elevations (e.g., non-continuous changes in thickness/diameter). In one or more embodiments, the jacket features may include a varying output geometry (e.g., a taper) of an outer surface of the jacket.

These externally added three-dimensional surface features of the jacket, as described herein, may aid in performance of a medical device or delivery system by, e.g., modifying the friction of interface surfaces between the medical device body and the anatomy of the patient, creating anchoring mechanisms for screwing or threading the medical device into an annular/cylindrical anatomical feature, or creating preferential performance characteristics (e.g., bending, straightening, torque, etc.).

Furthermore, these jacket features may be formed by any suitable tools. For example, the tools and process herein may provide a way to design and develop medical device features and methods of making the same. Specifically, as described herein, the jacket may be altered by adjusting the shaped and/or size of the jacket using a shutter, the jacket may be altered by trimming a portion of the jacket using one or more cutting tools, the jacket may be altered by depositing an additional filament on the jacket using an additional guide sheath, the jacket may be altered by imprinting a texture onto the jacket using one or more rolling wheels, etc.

Thus, various embodiments described herein are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

What is claimed is:

1. A medical device in the form a catheter/lead, the medical device comprising:
   an elongated catheter body extending along a catheter axis; and
   a pull wire extending along the catheter body, the pull wire located within the catheter body and extending to an anchor at a distal end of the pull wire, wherein a location of the pull wire varies relative to the catheter axis when the pull wire is in a relaxed state such that the location of the pull wire relative to the catheter axis exhibits a first change radially toward or away from the catheter axis along a first section of the elongated catheter body and exhibits a second change radially toward or away from the catheter axis along a second section of the elongated catheter body, the first change differing from the second change, wherein the pull wire is configured to deflect the catheter body in two or more planes when pulled in a direction away from the anchor.

2. The medical device according to claim 1, wherein the pull wire comprises the only pull wire located in the catheter body.

3. The medical device according to claim 1, wherein, relative to the catheter axis and over a selected portion of a length of the catheter body extending from a start location to a finish location, the pull wire moves, from the start location to the finish location over the selected portion, over an arc of 1 degree or more, 2 degrees or more, 3 degrees or more, 4 degrees or more, or 5 degrees or more at a low end, and X+(n*360) degrees or less at an upper end, where X is 360 degrees or less, 330 degrees or less, 300 degrees or less, 270 degrees or less, 240 degrees or less, 210 degrees or less, 180 degrees or less, 150 degrees or less, 135 degrees or less, 120 degrees or less, 90 degrees or less, 75 degrees or less, 60 degrees or less, 45 degrees or less, 30 degrees or less, 15 degrees or less, 10 degrees or less, or 5 degrees or less and n is 0, 1, 2 or more.

4. The medical device according to claim 1, wherein:
   at a first location along a length of the catheter body, the pull wire is located at a first clock position within the catheter relative to the catheter axis;
   at a second location distal from the first location, the pull wire is located at a second clock position that is offset from the first clock position within the catheter relative to the catheter axis; and
   at a third location distal from the second location, the pull wire is located at a third clock position that is offset from the second clock position within the catheter relative to the catheter axis.

5. The medical device according to claim 1, wherein:
   at a first location along a length of the catheter body, the pull wire is located at a first radial position within the catheter relative to the catheter axis;
   at a second location distal from the first location, the pull wire is located at a second radial position within the catheter relative to the catheter axis that is different than the first radial position; and
   at a third location distal from the second location, the pull wire is located at a third radial position within the catheter relative to the catheter axis that is different than the second radial position.

6. The medical device according to claim 3, wherein the selected portion comprises 50% or less, 40% or less, 30% or less, 20% or less, or 10% or less of a total length of the catheter body as measured from the proximal end to the distal end.

7. The medical device according to claim 4, wherein a first rate of change in clock position between the first clock position and the second clock position is different from a second rate of change in clock position between the second clock position and the third clock position, wherein rate of change in clock position refers to amount of clock position change over a unit of distance along the elongated catheter body.

8. The medical device according to claim 5, wherein a first rate of change in radial position between the first radial position and the second radial position is different from a second rate of change in radial position between the second radial position and the third radial position, wherein rate of change in radial position refers to amount of radial position change over a unit of distance along the elongated catheter body.

9. A medical device in the form a catheter/lead, the medical device comprising:
   an elongated catheter body extending along a catheter axis; and
   a pull wire extending along the catheter body, the pull wire located within the catheter body and extending to an anchor at a distal end of the pull wire, wherein a location of the pull wire varies relative to the catheter axis when the pull wire is in a relaxed state such that the location of the pull wire relative to the catheter axis exhibits a first change relative to the catheter axis along a first section of the elongated catheter body and exhibits a second change relative to the catheter axis along a second section of the elongated catheter body, the first change differing from the second change, wherein the pull wire is configured to deflect the catheter body in two or more planes when pulled in a direction away from the anchor, wherein the first and second changes in location of the pull wire are changes in location both radially toward or away from the catheter axis and circumferentially around at least a portion of the catheter body with respect to distance along the elongated catheter body.

10. A medical device in the form a catheter/lead, the medical device comprising:
   an elongated catheter body extending along a catheter axis; and
   a pull wire extending along the catheter body, the pull wire located within the catheter body and extending to an anchor at a distal end of the pull wire, wherein a location of the pull wire varies with distance along the elongated catheter body when the pull wire is in a relaxed state such that the location of the pull wire changes radially toward or away from the catheter axis with respect to distance along the elongated catheter body, wherein the changes of the radial location of the pull wire are configured such that the catheter body is deflected in two or more planes when the pull wire is pulled in a direction away from the anchor.

11. The medical device according to claim 10, wherein the pull wire comprises the only pull wire located in the catheter body.

12. A medical device in the form a catheter/lead, the medical device comprising:
   an elongated catheter body extending along a catheter axis; and
   a pull wire extending along the catheter body, the pull wire located within the catheter body and extending to an anchor at a distal end of the pull wire, wherein a location of the pull wire varies relative to the catheter axis when the pull wire is in a relaxed state such that the location of the pull wire relative to the catheter axis exhibits a first change relative to the catheter axis along a first section of the elongated catheter body and exhibits a second change relative to the catheter axis along a second section of the elongated catheter body, the first change differing from the second change, wherein the pull wire is configured to deflect the catheter body in two or more planes when pulled in a direction away from the anchor,
   wherein the first and second changes are changes in location of the pull wire around at least a portion of the circumference of the catheter body and along the elongated catheter body, and wherein the first change in location of the pull wire is a clockwise change in circumferential location over the first section of the elongated catheter body and the second change in location of the pull wire is a counterclockwise change in circumferential location over the second section of the elongated catheter body.

* * * * *